(12) United States Patent
Noda et al.

(10) Patent No.: US 9,452,978 B2
(45) Date of Patent: Sep. 27, 2016

(54) CHAIN TRANSFER AGENT AND EMULSION POLYMERIZATION USING THE SAME

(75) Inventors: Tetsuya Noda, Otake (JP); Fuminori Nakaya, Otake (JP); Keiichi Sakashita, Otake (JP); Yosuke Matsunaga, Otake (JP); Taeko Oonuma, Otake (JP); Yoshiko Irie, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 675 days.

(21) Appl. No.: 13/575,775

(22) PCT Filed: Jan. 27, 2011

(86) PCT No.: PCT/JP2011/051649
§ 371 (c)(1),
(2), (4) Date: Jul. 27, 2012

(87) PCT Pub. No.: WO2011/093401
PCT Pub. Date: Aug. 4, 2011

(65) Prior Publication Data
US 2012/0309900 A1    Dec. 6, 2012

(30) Foreign Application Priority Data

Jan. 27, 2010 (JP) ................................ 2010-015546

(51) Int. Cl.
| C08F 2/38 | (2006.01) |
| C07C 327/36 | (2006.01) |
| C07F 9/09 | (2006.01) |
| C08F 2/22 | (2006.01) |
| C08F 293/00 | (2006.01) |

(52) U.S. Cl.
CPC ............. *C07C 327/36* (2013.01); *C07F 9/091* (2013.01); *C08F 2/22* (2013.01); *C08F 2/38* (2013.01); *C08F 293/005* (2013.01); *C08F 2438/03* (2013.01)

(58) Field of Classification Search
CPC .. C08F 2438/03; C08F 2/38; C08F 293/005; C07C 327/36
See application file for complete search history.

(56) References Cited

U.S. PATENT DOCUMENTS

| 4,048,311 A | 9/1977 | Berges |
| 4,066,762 A | 1/1978 | Dunn |
| 4,220,644 A | 9/1980 | Berges |
| 4,533,467 A | 8/1985 | Kimble et al. |
| 7,064,151 B1 * | 6/2006 | Berge ................. C08F 293/005 521/142 |
| 7,625,985 B1 | 12/2009 | Parker et al. |
| 2003/0120101 A1 | 6/2003 | Lai |
| 2003/0191262 A1 * | 10/2003 | McCormick .......... C07C 327/36 526/288 |
| 2006/0223936 A1 | 10/2006 | Such et al. |
| 2007/0167571 A1 | 7/2007 | Lai |
| 2007/0179262 A1 | 8/2007 | Suau et al. |
| 2007/0299221 A1 | 12/2007 | Perrier |
| 2011/0207881 A1 | 8/2011 | Charleux et al. |

FOREIGN PATENT DOCUMENTS

| CN | 101591403 A | 12/2009 |
| EP | 0 052 442 A1 | 5/1982 |
| EP | 1 801 100 A1 | 6/2007 |
| EP | 2 511 028 A1 | 10/2012 |
| FR | 2 868 068 | 9/2005 |
| FR | 2 931 154 | 11/2009 |
| GB | 1 274 521 | 5/1972 |
| GB | 1 309 743 | 3/1973 |
| JP | 12-06338 | 8/1989 |
| JP | 2005 513252 | 5/2005 |
| JP | 2007 515538 | 6/2007 |
| JP | 2007 169634 | 7/2007 |
| WO | WO 00/42006 | 7/2000 |
| WO | 02/055185 A2 | 7/2002 |
| WO | 03/055919 A1 | 7/2003 |

OTHER PUBLICATIONS

Benaglia et al. Macromolecules 2005.*
Kanagasabapathy et al. Macromol Rapid Commun. 2001.*
Tong Journal of POlymer Science Part A 200.*
Combined Chinese Office Action and Search Report Issued May 6, 2013 in Patent Application No. 201180007390.X (with English translation of Categories of Cited Documents).
Combined Chinese Office Action and Search Report issued Jan. 13, 2014, in Patent Application No. 201180007390.X.

(Continued)

*Primary Examiner* — Mark Kaucher
(74) *Attorney, Agent, or Firm* — Oblon, McClelland, Maier & Neustadt, L.L.P

(57) ABSTRACT

To provide a novel compound having both a surface-activating ability and a polymerization controlling ability.

A compound represented by the following general formula (1) or (2):

$$\left( R^1 \diagdown Z \diagdown \underset{\underset{S}{\|}}{C} \diagdown S \right)_p R^2 \quad (1)$$

$$R^3 \left( Z \diagdown \underset{\underset{S}{\|}}{C} \diagdown S \diagdown R^4 \right)_q \quad (2)$$

wherein, $R^1$ and $R^3$ are an organic group having the hydrophile-lipophile balance (HLB) determined by Griffin's method of 3 or more. The definitions of $R^1$, $R^2$, $R^3$, $R^4$, Z, p and q are described in the Description.

12 Claims, 6 Drawing Sheets

(56) References Cited

OTHER PUBLICATIONS

Maria C. Lechmann, et al., "Functional Templates for Hybrid Materials with Orthogonal Functionality", Langmuir, vol. 25, No. 17, 2009, pp. 10202-10208.

Xuewei Xu, et al., "Synthesis of Well-Defined, Brush-Type, Amphiphilic [Poly(styrene-co-2-hydroxyethyl methacrylate)-graft-Poly(ε-caprolactone)]-b-Poly(ethylene oxide)-b-[Poly(styrene-co-2-hydroxyethyl methacrylate)-graft-Poly(ε-caprolactone)] and Its Aggregation Behavior in Aqueous Media", Journal of Polymer Science: Part A: Polymer Chemistry, vol. 44, Issue 15, Aug. 1, 2006, pp. 4396-4408.

Xuewei Xu, et al., "Synthesis and Characterization of Amphiphilic Copolymer of Linear Poly(ethylene oxide) Linked with [Poly(styrene-co-2-hydroxyethyl methacrylate)-graft-Poly(ε-caprolactone)] Using Sequential Controlled Polymerization", Journal of Polymer Science: Part A: Polymer Chemistry, vol. 44, 2006, pp. 467-476.

Fuqiang Lan, et al., "Synthesis of Amphiphilic Star-Brush Copolymer $PEO_4$-b-[P(St-co-HEMA)-g-PCL]$_4$", China Academic Journal Electronic Publishing House, http://www.cnki.net, 1994-2014, pp. 90-95 (with English translation).

Ezio Rizzardo, et al., "RAFT Polymerization: Adding to the Picture", Macromol. Symp., vol. 248, 2007, pp. 104-116.

Yen K. Chong, et al., "Thiocarbonylthio End Group Removal from RAFT-Synthesized Polymers by Radical-Induced Reduction", Macromolecules, vol. 40, No. 13, 2007, pp. 4446-4455.

Sébastien Perrier, et al., "Reversible Addition-Fragmentation Chain Transfer Polymerization: End Group Modification for Functionalized Polymers and Chain Transfer Agent Recovery", Macromolecules, vol. 38, No. 6, 2005, pp. 2033-2036.

The Extended European Search Report issued Sep. 10, 2014, in Application No. / Patent No. 11737112.0-1454/2530073.

Arenal L., et al., "Reaction of 5(4H)-Thiazolones With Diazomethane", Database Reaxys, [Online], Elsevier Properties SA, Tetrahedron; vol. 39; nb. 8;, XP-002728722, XRN=2353368, XRN=2562206, 1983, 1 page (submitting English Abstract only).

Siegfried, et al., Database Reaxys, [Online], Elsevier Properties SA, Hoppe-Seyler's Zeitschrift fuer Physiologische Chemie; vol. 70;, XP-002728723, XRN=2279995, XRN=2562206, XRN=2758869, XRN=3142353, XRN=3152617, XRN=3404368, XRN=3793619, XRN=3801679, XRN=3617625, XRN=3818570, 1910, 1 page, (submitting English Abstract only).

Schaumann,E., et al., Database Reaxys, [Online], Elsevier Properties SA, Chemische Berichte; vol. 111;, XP-002728724, XRN=2087430, 1978, 1 page, (submitting English Abstract only).

Sjoeberg,B. et al., Database Reaxys, [Online], Elsevier Properties SA, Acta Chemica Scandinavica (1947-1973); vol. 16;, XP-002728725, XRN=6125088, XRN=6128645, XRN=6131089, 1962, 1 page, (submitting English Abstract only).

Barrett,G.C., et al., Database Reaxys, [Online], Elsevier Properties SA, Journal of the Chemical Society, Chemical Communications, XP-002728726, XRN=2364581, XRN=6123389, 1972, 1 page, (submitting English Abstract only).

Berges;et al., Database Reaxys, [Online], Elsevier Properties SA, "4,5-Dihydro-5-thioxo-1H-tetrazole-1-alkanoic and alkanesulfonic acids and their amide derivatives", Journal of Heterocyclic Chemistry; vol. 15; nb. 6;, XP-002728727, XRN=2083037, XRN=2085107, XRN=2087903, XRN=2095151, XRN=2433715, 1978, 1 page, (submitting English Abstract only).

LiBassi,G. et al., Database Reaxys, [Online], Elsevier Properties SA, Gazzetta Chimica Italiana; vol. 107, XP-002728728, XRN=6589672, XRN=6589673, XRN=6590709, XRN=6590710, 1977, 1 page, (submitting English Abstract only).

Holland, et al., Database Reaxys, [Online], Elsevier Properties SA, Journal of the Chemical Society, XP-002728729, XRN=3315699, XRN=3409468, XRN=3793351, 1958, 1 page, (submitting English Abstract only).

Sjoeberg et al., Database Reaxys, [Online], Elsevier Properties SA, Journal of the American Chemical Society; vol. 81;, XP-002728730, XRN=1709191, 1 page, (submitting English Abstract only), Date: 1959.

Velluz et al., Database Reaxys, [Online], Elsevier Properties SA, Opt.Circular Dichroism;, XP-002728731, XRN=3989362, XRN=2444847, 1965, 2 page, (submitting English Abstract only).

Himmelreich., et al.,"NMR-Spectroscopic Investigation of E/Z-Isomerism in Substituted Dithlocarbacinic Acid Derivatives" Database Reaxys, [Online], Elsevier Properties SA, Monatshefte fuer Chemie; vol. 121; nb. 11;, XP-002728732, XRN=4292563, XRN=4292564, XRN=4292565, 1990, 1 page, (submitting English Abstract only).

Mikitenko,et al., "Condensed Heterocycles With a Thiazole Ring. 6. New Method for the Preparation of Imidazo<1.2-c>Thiazolium and Thiazolo<3.4-a>Pyridinium Salts" Database Reaxys, [Online], Elsevier Properties SA, Chemistry of Heterocyclic Compounds (New York. NY, United States); vol. 19; nb. 7;, Khimiya Geterotsiklicheskikh Soedinenii; vol. 19; nb. 7;, XP-002728733, XRN=2353368, XRN=2357914, XRN=2433715,XRN=4440166, 1983, 1 page, (submitting English Abstract only).

Kovtun, et al., "Condensed Heterocyclic Systems with a Thiazole Ring. 11. Thiazolo<3,4-b>-I,2,4- Triazinones", , Database Reaxys, [Online], Elsevier Properties SA, Chemistry of Heterocyclic Compounds (New York, NY, United States); vol. 21; nb. 11; Khimiya Geterotslkllcheskikh Soedinenli; vol. 21; nb. 11;, XP-002728734, XRN=2274810, XRN=4292563, XRN=44427, 1985, 1 page (submitting English Abstract only).

Saiga, et al., "Synthesis of 1, 2, 3, 4-tetrahydro-β-carboline derivatives as hepatoprotective agents. I. Dlthiocarbamates of several α-amino acids", Database Reaxys, [Online], Elsevier Properties SA, Chemical and Pharmaceutical Bulletin; vol. 35; nb. 7;, XP-002728735, XRN=5979704, 1987, 1 page (submitting English Abstract only).

Ware Jr., et al., "Evaluation of new L-thlocitrulline derivatives as Inhibitors of nitric oxide synthase", Database Reaxys, [Online], Elsevier Properties SA, Bioorganic and Medicinal Chemistry Letters;—vol. 10; nb. 24;, XP-002728736, XRN=8767652, 2000, 1 page (submitting English Abstract only).

Vaillancourt, et al., "Synthesis and biological activity of amlnoguanidine and diamlnoguanidine analogues of the antidiabetic/antiobesity agent 3-guanidinoproplonic acid" Database Reaxys, [Online], Elsevier Properties SA, Journal of Medicinal Chemistry; vol. 44; nb. 8;, XP-002728737, XRN=1709191, XRN=2083037, XRN=2433715, XRN=6123389, XRN=8830131, XRN=8 833929, XRN=8837454, 2001 1 page (submitting English Abstract only).

Mevellec, et al., "Novel six-coordinate oxorhenium(V) '3+2' mixed-ligand complexes carrying the SNO/SN donor atom set", Database Reaxys, [Online], Elsevier Properties SA, Inorganica Chimlca Acta; yol. 332; nb. 1;, XP-002728738, XRN=17626979, 2002, 1 page (submitting English Abstract only).

Berges, et al., "4,5-Dlhydro-S-thloxo-1H-tetrazole.1-alkanolc and alkanesulfonlc acids and their amide derivatives", Database Reaxys, [Online], Elsevier Properties SA, Journal of Heterocyclic Chemistry; vol. 15; nb. 6:, XP-002728739, XRN=2089748, XRN=2089748, XRN=2096193, XRN=2104198, XRN=6128628, XRN=6128761, XRN=6128862, XRN=6128989, 1978, 1 page (submitting English Abstract only).

Lindquist, et al., "Tridentatols D-H. nematocyst metabolites and precursors of the activated chemical defense in the marine hydroid Trldentata marginata (Klrchenpauer 1864)", Database Reaxys, [Online], Elsevier Properties SA, Journal of Natural Products; vol. 65; nb. 5, XP-002728740, XRN=9167797, 2002, 1 page (submitting English Abstract only).

Zhu, J.L., et al., "Novel polycationic micelles for drug delivery and gene transfer," Journal of Materials Chemistry, 18 (37), pp. 4433 to 4441, (2008).

International Search Report Issued Mar. 8, 2011 in PCT/JP11/51649 Filed Jan. 27, 2011.

Partial Search Report issued Jul. 24, 2015 in European Patent Application No. 15161425.2.

Fozi M. Saud, et al, "Magnetite Nanoparticles for the Preparation of Ultrapure RAFT Polymers", Macromolecules, vol. 41, 2008, pp. 1598-1600.

Gotthardt H., et al., "2,2'-Bridged bis(thiophenes) from bis(1,3-dithiolylium-4-olates) and alkynes", "Synthese und Physikalishe

(56) References Cited

OTHER PUBLICATIONS

Eigenshaften Neur 2,2'-verbrueckter bis(1,3-dithiolylium-4olate)// Synthesis and Physical Properties of Novel 2,2'-bridged bis(1,3-dithiolylium-4-olates)", Chemischte Beriche, VCH, DE, vol. 120, No. 1, 1987, XP-002741944, 2 pages (English derwent abstract only).

Guy Levesque, et al., "Protein Thioacylation. 1. Reagents Design and Synthesis", Biomacromolecules, American Chemical Society, US, vol. 1, No. 3, Sep. 21, 2000, 1, XP-001155684, pages 387-399.

Hans Gotthardt, et al., Synthese und physikalische Eigenschaften neuer 2,2'-verbrückter Bis(1,3-dithiolylium-4-olate), Chem. Ber. 120, 1987, XP009063495, pp. 61-66.

N.H. Leon, et al., "Novel Polymers Containing Thiocarbonyl Groups", Polymers Letters Edition, vol. 12, 1974, XP002741942, pp. 693-696.

Decision of Reexamination issued Jan. 15, 2016, in Chinese Patent Application No. 201180007390.X filed Jan. 27, 2011 (with English translation).

Notification of Reexamination issued Sep. 23, 2015, in Chinese Patent Application No. 201180007390X (with English translation).

Glatzel, et al., "Well-defined synthetic polymers with a protein-like gelation behavior in water", Chem. Commun., vol. 46, pp. 4517-4519 (2010).

Baussard, et al., "New chain transfer agents for reversible addition-fragmentation chain transfer (RAFT) polymerisation in aqueous solution", Polymer, vol. 45, pp. 3615-3626 (2004).

Holmberg, Bror, "Propiorhodanines", Berichte der Deutschen Chemischen Gesellschaft, vol. 47, pp. 159-165 (1914), Abstract only XP-002745784.

Runge, et al., "Trithiocarbonic acid. I. Aliphatic and arylaliphatic trithiocarbonic acid diesters", Journal fuer Praktische Chemie (Leipzig), vol. 7, pp. 268-278 (1959), Abstract only XP-002745785.

Iliceto, et al., "Preparation of organic compounds labeled with S35. A convenient method for obtaining labeled isothiocyanates", Gazzetta Chimica Italiana, vol. 89, pp. 1950-1955 (1959), Abstract only XP-002745786.

Hiltunen, et al., "New Associative EHEC-g -PAam Copolymers: Their Syntheses, Characterization, and Rheological Behavior", Journal of Polymer Science: Part B: Polymer Physics, vol. 47, pp. 1869-1879 (2009) XP-002745787.

Chen, et al., "Thiocarbonylthio End Group Removal from RAFT-Synthesized Polymers by a Radical-Induced Process", Journal of Polymer Science: Part A: Polymer Chemistry, vol. 47, pp. 6704-6714 (2009) XP-002745788.

Willcock, et al., "End group removal and modification of RAFT polymers", Polym. Chem., vol. 1, pp. 149-157 (2010) XP-002745791.

Cao, et al., "Cleavage of Polystyrene-*b*-Poly(ethylene oxide) Block Copolymers with a Trithiocarbonate Linkage in Solutions", Journal of Polymer Science: Part A: Polymer Chemistry, vol. 48, pp. 3834-3840 (2010) XP-002745792.

\* cited by examiner

CHAIN TRANSFER AGENT AND EMULSION POLYMERIZATION USING THE SAME

FIELD OF THE INVENTION

The present invention relates to a RAFT agent having a surface-activating ability and a polymerization-controlling ability, more specifically emulsion polymerization using said RAFT agent, and a polymer obtained therefrom.

BACKGROUND OF THE INVENTION

Polymers having narrow molecular weight distribution have characteristics of having low viscosity compared to polymers having broad molecular weight distribution with the same number-average molecular weight. Block copolymers, compared to random copolymers, retain physical and chemical characteristics carried by each block, and for example water soluble-nonwater soluble diblock copolymers, similarly to low molecular weight emulsifying agents, have characteristics of forming micelles in an aqueous solution with the water soluble block facing the aqueous phase and the nonwater soluble block as the core. In order to obtain polymers and block copolymers having narrow molecular weight distribution, a sophisticated function of controlling polymerization is required.

As a polymerization method having a sophisticated function of controlling polymerization for obtaining a polymer and a block copolymer having narrow molecular weight distribution, living radical polymerization (sometimes referred to as "controlled radical polymerization") is known. Depending on the mechanism of polymerization, several types of polymerization methods are known. Among them, a polymerization mechanism in which chain transfer during polymerization proceeds reversibly is useful as a polymerization method to obtain a polymer and a block copolymer having narrow molecular weight distribution. As such a polymerization method, reversible addition-fragmentation chain transfer (hereinafter referred to as "RAFT") polymerization has been proposed.

As a method of producing polymers, from the viewpoint of industrial production, emulsion polymerization is superior in terms of removing reaction heat and recovering polymers, and thus techniques of carrying out controlled radical polymerization using emulsion polymerization may be desired. Various investigations have been made on emulsion polymerization that employs "RAFT agent," a polymerization controlling agent that permits RAFT polymerization. In emulsion polymerization, however, an emulsifying agent in addition to a RAFT agent must generally be added, which in many cases may markedly reduce polymerization speed or reduce latex stability. Thus, in emulsion polymerization that requires the addition of an emulsifying agent in addition to the RAFT agent, it is known that its ability of controlling molecular weight is poorer than the homogeneous solution polymerization, and thus there is a need for a RAFT agent that acts not only as an emulsifying agent but also as a polymerization controlling agent.

Patent Document 1 illustrates a compound that serves as both an emulsifying agent and a polymerization initiator. However, the molecular weight distribution shown in the Examples of Patent Document 1 has a very broad range, and thus it cannot be recognized to be superior to molecular weight distribution in an emulsion polymerization that does not use controlled polymerization.

In Patent Document 2 and Non-patent documents 1 and 2, RAFT agents having introduced therein polyethylene glycol (PEG) units having a surface-activating ability are reported. However, in polymerization using this RAFT agent, PEG units may inevitably be introduced into the ends of the polymer obtained, and though sulfur-containing units (derived from a RAFT agent; they are dithioester sites in many cases) that cause coloration can be removed during the post-treatment step using a radical-generating agent such as an azo compound and a peroxide, or an amine, it is difficult to remove PEG units as well that are sites having a surface-activating ability (hereinafter referred to as "surface-active sites"). As a result, polymers containing residual PEG units may pose a problem of water absorptivity depending on the intended uses.

PRIOR TECHNICAL DOCUMENTS

Patent Documents

Patent Document 1: Kohyo (Japanese PCT Patent Publication) No. 2002-534499
Patent Document 2: Kokai (Japanese Unexamined Patent Publication) No. 2003-147312

Non-Patent Documents

Non-patent document 1: Macromolecules, 2008, Vol. 41, pp. 4065-4068
Non-patent document 2: Macromolecules, 2009, Vol. 42, pp. 946-956

SUMMARY OF THE INVENTION

Problems to be Solved by the Invention

The problem to be solved by the present invention is to provide a novel compound that plays the role of both surface-activating ability and polymerization controlling ability. Another problem is to provide a polymerization method that can control polymerization until it reaches a high conversion ratio. Another problem is to provide a polymerization method that facilitates the synthesis of block copolymers. Furthermore, another problem is to provide a polymerization method that permits the removal of surface active sites and sulfur-containing units that cause coloration during the post-treatment after polymerization.

Means to Solve the Problems

After intensive research, the present inventors have found that by designing an unprecedented RAFT agent in which a structure having a surface-activating ability has been introduced into a specific site of the RAFT agent, emulsion polymerization can be realized, and sulfur-containing units can be easily removed after polymerization.

Thus, by emulsifying a RAFT agent represented by the following general formula and a vinyl monomer in an aqueous medium, followed by radical polymerization, polymerization control up to a high conversion ratio may become possible, and block copolymers can also be synthesized. Furthermore, by dissociating the chemical bond between the RAFT agent and the polymer after polymerization, the RAFT agent can be removed from the polymer.

Furthermore, from said polymer obtained by removing the RAFT agent by the above method, surface active sites can also be removed by treatment after polymerization, and the polymer obtained can also be used as a thermoplastic resin composition.

Effects of the Invention

Emulsion polymerization that uses a RAFT agent having a surface-activating ability of the present invention has an advantage that not only can it enable polymerization control but RAFT agent units having a surface-activating ability can be removed from the polymer.

MODE FOR CARRYING OUT THE INVENTION

Figure 1:
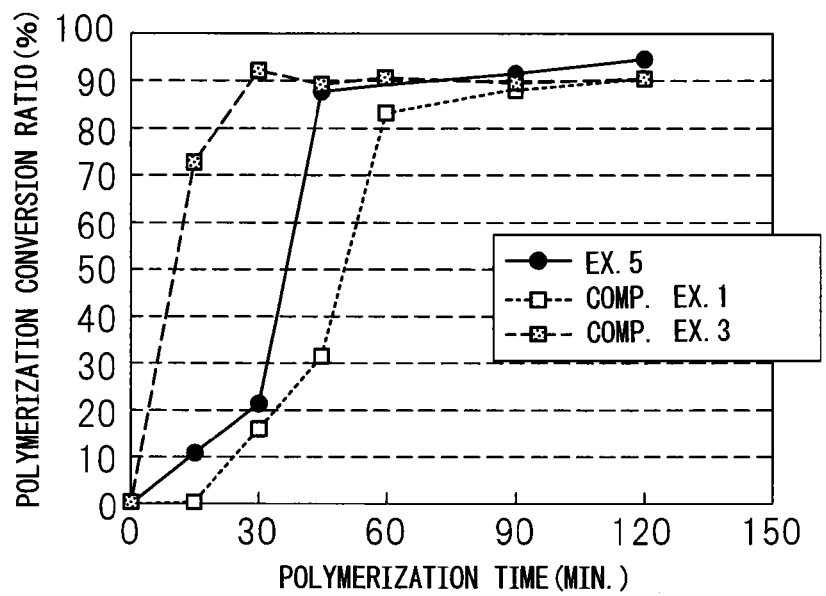
FIG. 1 A graph plotting the relationship between the polymerization time and the polymerization conversion ratio obtained in Working Example 5, Comparative Example 1 and Comparative Example 3.

When a compound represented by a thiocarbonylthio compound is added into the radical polymerization system, it can act as a radical polymerization chain transfer agent. As such a compound, there can be mentioned, for example, a compound having a thiocarbonylthio group (a dithioester structure or a trithiocarbonate structure). The greater the chain transfer constant relative to vinyl monomers to be polymerized, RAFT polymerization may proceed while being controlled and the narrower the molecular weight distribution of the polymer becomes. Representative reaction mechanisms are shown below. The RAFT polymerization is described in, for example, "HANDBOOK OF RADICAL POLYMERIZATION," K. Matyjaszewski and T. P. Davis Ed., Wiley, 2002, on page 661 and after. As used herein, M in the reaction mechanism shown below represents a vinyl monomer, and Pm and Pn represent m-mer and n-mer polymer, respectively.

$k_i$, $k_t$, $k_{add}$, $k_{-add}$, $k_\beta$, $k_{-\beta}$, $k_{addp}$ and $k_{-addp}$ represent the rate constant of respective reactions. R and Z are different from the R and Z in the compounds represented by the general formula (1) to (6) below, and are signs used to clearly explain the reaction mechanisms. A compound represented by a thiocarbonylthio compound added to control polymerization by such a mechanism is called a RAFT agent.

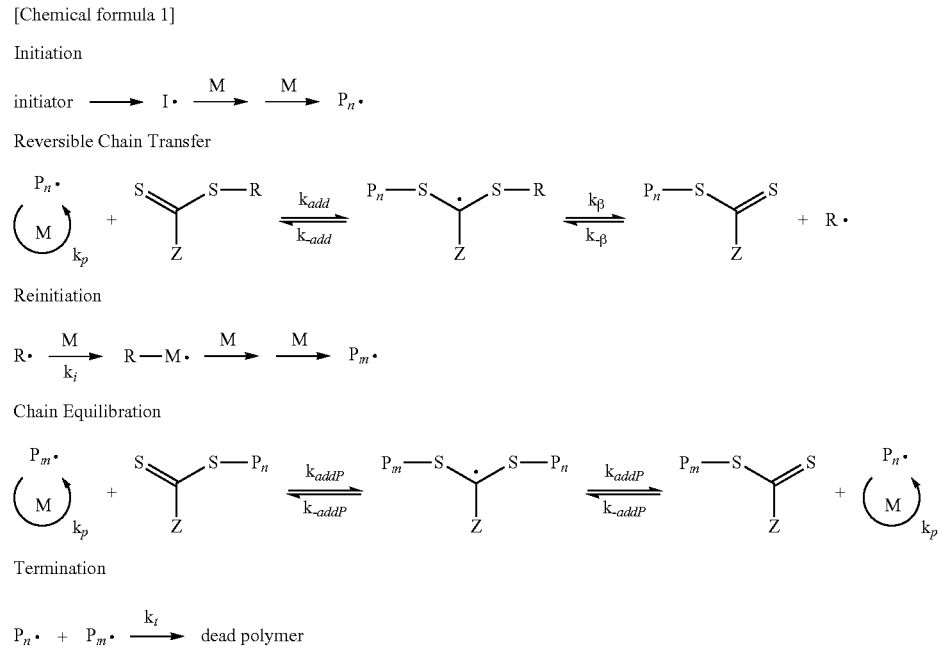

[Chemical formula 1]

The compound of the present invention is a compound having a surface-activating ability, and a compound that permits controlled radical polymerization by being added as a RAFT agent into the polymerization system.

Thus, it is a compound represented by the following general formula (1) or (2):

[Chemical formula 2]

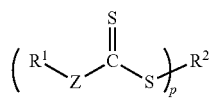
(1)

[Chemical formula 3]

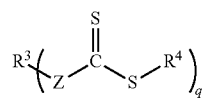
(2)

wherein, $R^1$ and $R^3$ each represent an organic group having a hydrophile-lipophile balance (HLB) determined by Griffin's method of 3 or more, Z represents a nitrogen atom, an oxygen atom, a sulfur atom, a methylene group, or an unsubstituted aromatic hydrocarbon group, $R^1$ represents, when Z is other than a sulfur atom, a monovalent organic group having one or more carbons, and said monovalent organic group may comprise at least one of a nitrogen atom, an oxygen atom, a sulfur atom, a halogen atom, a silicon atom and a phosphorous atom and may represent a high molecular weight substance, $R^1$ represents, when Z is a sulfur atom, a monovalent aliphatic hydrocarbon group or aromatic hydrocarbon group having one or more carbons that bind(s) to the sulfur atom at a primary carbon and said monovalent hydrocarbon group may comprise at least one of a nitrogen atom, an oxygen atom, a sulfur atom, a halogen atom, a silicon atom and a phosphorous atom, and may represent a high molecular weight substance; when a plurality of $R^1$ are present, they may be the same or different; and p is represented by an integer of 1 or more, $R^2$ is a p-valent organic group having one or more carbons, and said p-valent organic group may comprise at least one of a nitrogen atom, an oxygen atom, a sulfur atom, a halogen atom, a silicon atom, a phosphorous atom and a metal atom, and may represent a high molecular weight substance, $R^3$ represents, when Z is other than a sulfur atom, a q-valent organic group having one or more carbons, and the q-valent organic group may comprise at least one of a nitrogen atom, an oxygen atom, a sulfur atom, a halogen atom, a silicon atom and a phosphorous atom, and may represent a high molecular weight substance, $R^3$ represents, when Z is a sulfur atom, a monovalent aliphatic hydrocarbon group or aromatic hydrocarbon group having one or more carbons that bind(s) to the sulfur atom at a primary carbon; and q is an integer of 2 or more, and $R^4$ represents a monovalent organic group having one or more carbons, and the monovalent organic group may comprise at least one of a nitrogen atom, an oxygen atom, a sulfur atom, a halogen atom, a silicon atom, a phosphorous atom and a metal atom, and may represent a high molecular weight substance; and two or more of $R^4$ may be the same or different.

Griffin's method will be briefly explained below.

Griffin's method defines HLB value=20×(sum of the molecular mass of the hydrophilic portion/molecular weight), and at the HLB value of about 3-6, part of the molecule is dispersed in water and used as an emulsifier of water-in-oil (w/o) type emulsion. At the HLB value of about 6-8, the molecule, when well mixed, is dispersed in water to become milky and used as an emulsifier of w/o type emulsion and a wetting agent. At the HLB value of about 8-10, the molecule is stably dispersed in water to become a milky juice and used as a wetting agent and an emulsifier of o/w type emulsion. At the HLB value of about 10-13, the molecule is semitransparently dissolved in water and used as an emulsifier of o/w type emulsion. At the HLB value of about 13-16, the molecule is transparently dissolved in water and used as an emulsifier of o/w type emulsion and a detergent. At the HLB value of about 16-19, the molecule is transparently dissolved in water and used as a solubilizer. While the above HLB value relates to a molecule as a whole, in the present invention the HLB value is defined for a functional group as well in the following equation:

HLB value=20×(sum of the molecular mass of the hydrophilic portion in a functional group/molecular mass of the functional group)

When the HLB value for a functional group determined by Griffin's method is 3 or less, it means that the hydrophilicity is too low, and thus when subjected to emulsion polymerization, its polymerization controlling ability becomes poor thereby exhibiting a polymerization behavior similar to known RAFT agents. The maximum of the HLB value is 20 as can be seen from the defining equation.

Among the above compound (1) or (2), from the viewpoint of ease in synthesis and ease of polymerization control, Z may preferably be a sulfur atom, or a substituted or unsubstituted aromatic hydrocarbon, and more preferably an unsubstituted aromatic hydrocarbon. As $R^1$ and $R^3$, among the organic groups having a HLB value of 3 or more determined by Griffin's method, polyethylene glycol, polypropylene glycol, polyethylene glycol/polypropylene glycol block copolymers and derivatives thereof may be preferred, and those containing a carboxylic acid metal salt or sulfonic acid metal salt may be more preferred.

Whereas $R^2$ and $R^4$ are organic groups having one or more carbons that bind to the sulfur atom, among the organic groups having one or more carbons, those that can be eliminated by chain transfer may be preferred, and among them, those that can bind to the sulfur atom at the secondary carbon and those that can bind to the sulfur atom at the tertiary carbon may be preferred. Furthermore, those that can bind to the sulfur atom at the tertiary carbon may be more preferred because of their excellent controlling ability during the initial phase of polymerization. Substituents that can bind to the secondary or tertiary carbon may not be specifically limited as long as they do not inhibit polymerization, a substituted or unsubstituted hydrocarbon group, a substituted or an unsubstituted aromatic hydrocarbon, a cyano group and an ester group may be preferred. Among them, in terms of polymerization control, an unsubstituted hydrocarbon group, an unsubstituted aromatic hydrocarbon group and a cyano group may be preferred. The number of said substituents that bind to the secondary or tertiary carbon is two and three for the secondary or tertiary carbon, respectively, in which the type of said substituents may be different or the same. Specifically an organic group represented by the following formula may be preferred, and both of $R^{21}$ and $R^{22}$ may preferably be a methyl group.

[Chemical formula 4]

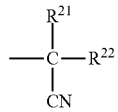

wherein $R^{21}$ and $R^{22}$ are the same or different alkyl groups having 1-8 carbons.

From the foregoing, among the compounds represented by compound (1) or (2), such compounds as are represented by (RAFT-1) to (RAFT-14) may be mentioned as preferred examples. As used herein, M illustrated in (RAFT-2), (RAFT-4) to (RAFT-10) represents a metal, preferably an alkali metal or an alkaline earth metal, and more preferably an alkali metal.

[Chemical formula 5]

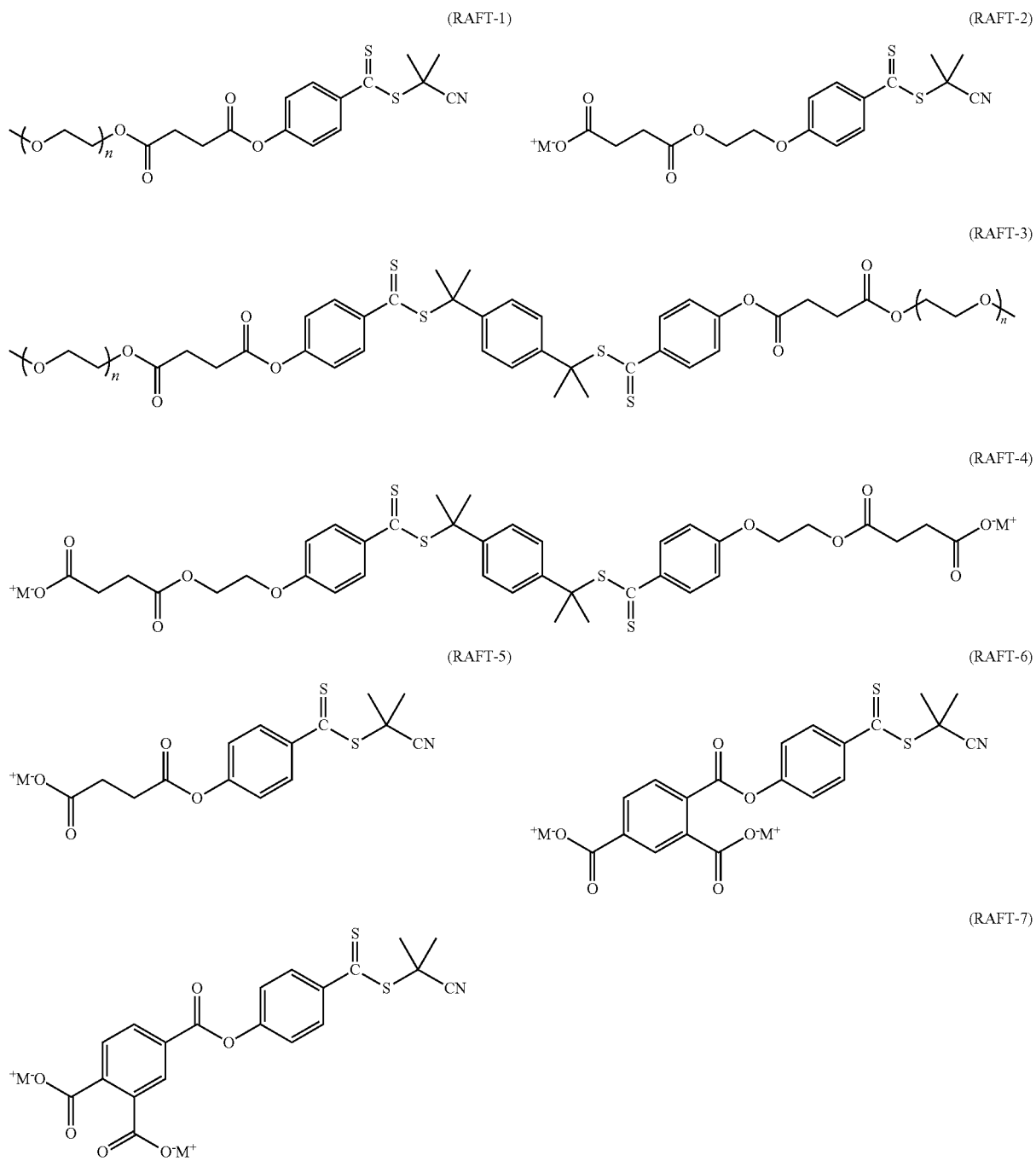

-continued
(RAFT-8)
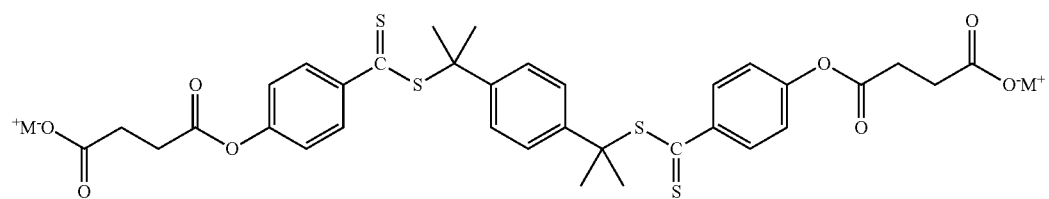
(RAFT-9)
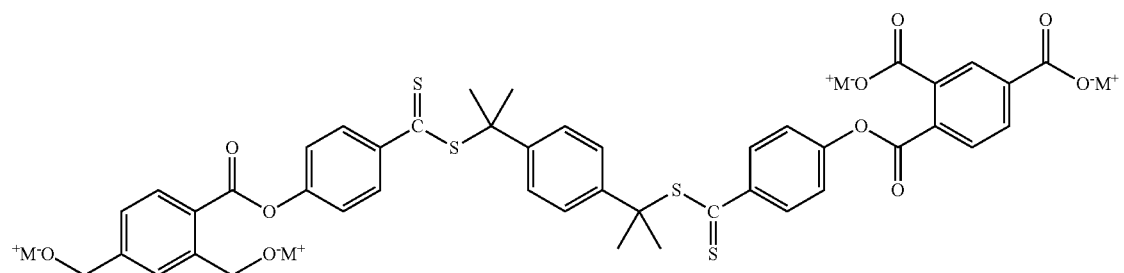
(RAFT-10)
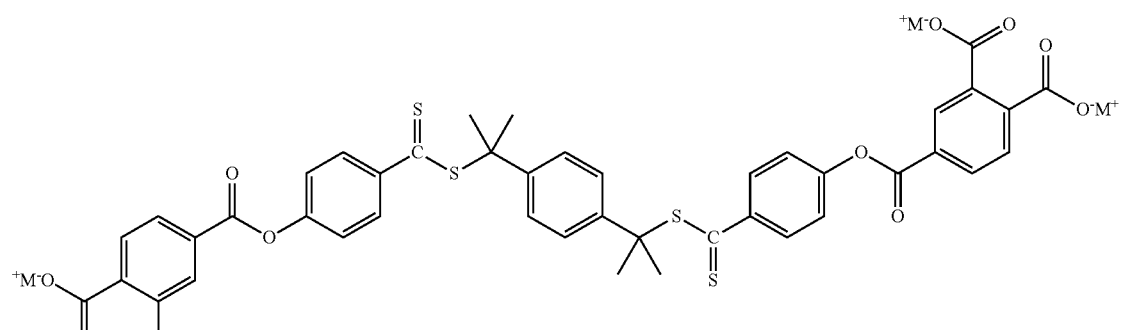
(RAFT-11)
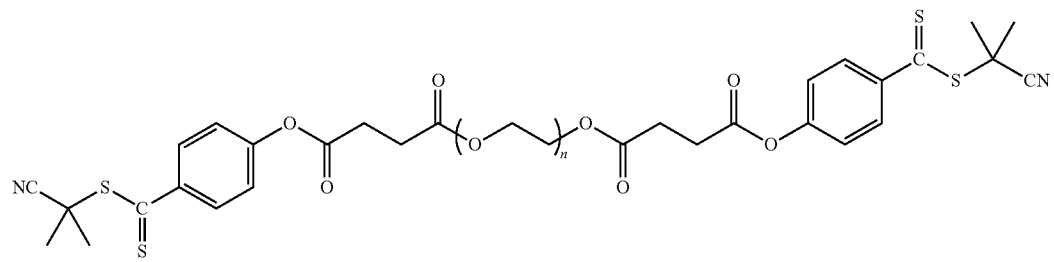
(RAFT-12)
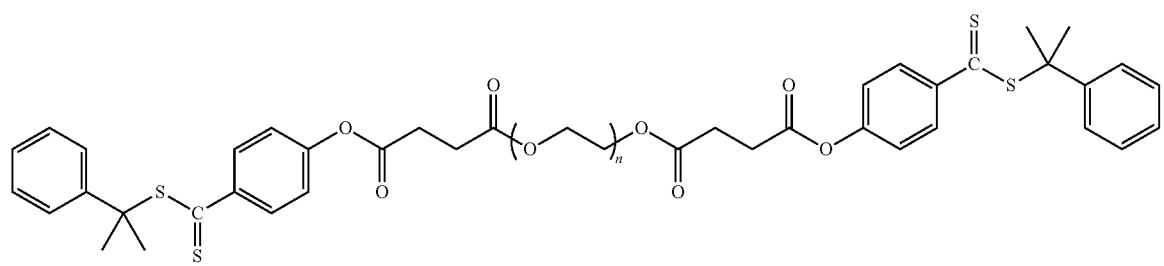
(RAFT-13)
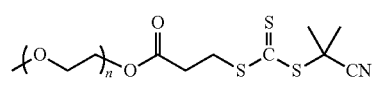
(RAFT-14)
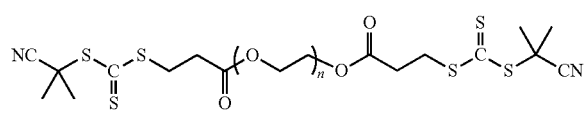

[Chemical formula 6]

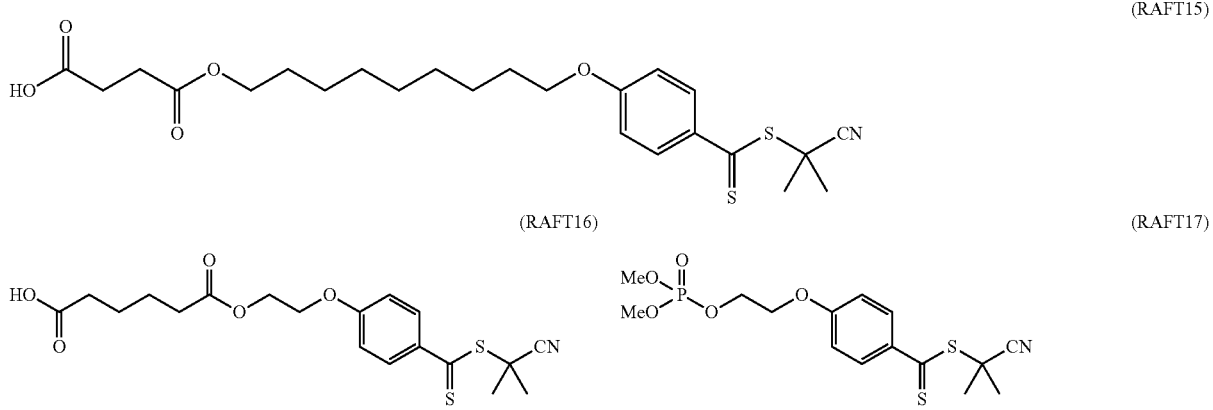

(RAFT15)

(RAFT16)

(RAFT17)

The above compound (1) or (2) may be synthesized by a known method. For example, in the synthesis of the above (RAFT-1), after protecting a hydroxy group of p-bromophenol, it is reacted with magnesium to synthesize a Grignard reagent, and then reacted with bromoisobutylnitrile. After deprotection, it is dehydration-condensed with a carboxylic acid-ended polyethylene glycol in which polyethylene glycol and succinic anhydride were reacted and thus (RAFT-1) of interest can be obtained. In the structure of (RAFT-1), Z corresponding to compound (1) is a phenyl group representing an aromatic hydrocarbon group.

In addition to the above, it can also be synthesized by a method in which after reacting p-bromophenol and polyethylene glycol, magnesium is reacted to synthesize a Grignard reagent, and then reacted with bromoisobutyronitrile to synthesize the compound.

In the structure of (RAFT-1), the molecular weight of polyethylene glycol corresponding to $R^1$ can be adjusted depending on the desired water solubility. When water solubility is desired to be increased, it can be adjusted by increasing the molecular weight of polyethylene glycol. The HLB value of $R^1$ when n=1 is about 5.0.

In the synthesis of (RAFT-2), after protecting a hydroxy group of p-bromophenol with chloroethanol, it is reacted with magnesium to synthesize a Grignard reagent, and then reacted with bromoisobutylnitrile. After further deprotection, it is reacted with succinic anhydride, and then the carboxylic acid may be neutralized with a metal hydroxide such as sodium hydroxide or a metal carbonate such as sodium carbonate, or a metal bicarbonate such as sodium bicarbonate to synthesize the compound. In the structure of (RAFT-2), Z corresponding to compound (1) is a phenyl group representing an aromatic hydrocarbon group, and when M is sodium, the HLB value of $R^1$ is about 11.7.

In the synthesis of (RAFT-3) or (RAFT-4) compounds, the reaction step of synthesizing a Grignard reagent may carried out in a manner similar to the synthesis of (RAFT-1) or (RAFT-2), and in stead of bromoisobutylnitrile it can be reacted with 1,4-di(bromoisopropyl)benzene to synthesize the compound. In the structure of (RAFT-3) or (RAFT-4), Z corresponding to compound (1) is a phenyl group representing an aromatic hydrocarbon group.

In the synthesis of (RAFT-6) or (RAFT-7) compounds, after protecting a hydroxy group of p-bromophenol, it is reacted with magnesium to synthesize a Grignard reagent, and then reacted with bromoisobutylnitrile. After deprotection, it is reacted with trimellitate anhydride, and then the carboxylic acid may be neutralized with a metal hydroxide such as sodium hydroxide or a metal carbonate such as sodium carbonate, or a metal bicarbonate such as sodium bicarbonate to synthesize the compound. In the structure of (RAFT-6) or (RAFT-7), Z corresponding to compound (1) is a phenyl group representing an aromatic hydrocarbon group, and when M is sodium, the HLB value of $R^1$ is about 11.1.

As a vinyl monomer for use in the present invention, there can be mentioned, for example, (meth)acrylic acid; a (meth) acrylate ester such as methyl (meth)acrylate, ethyl (meth) acrylate, n-propyl (meth)acrylate, isopropyl (meth)acrylate, allyl (meth)acrylate, n-butyl (meth)acrylate, isobutyl (meth) acrylate, sec-butyl (meth)acrylate, t-butyl (meth)acrylate, n-pentyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, nonyl (meth)acrylate, decyl (meth)acrylate, t-butylcyclohexyl (meth)acrylate, dodecyl (meth)acrylate, stearyl (meth)acrylate, isobornyl (meth)acrylate, phenyl (meth)acrylate, toluoyl (meth)acrylate, benzyl (meth)acrylate, 2-methoxyethyl (meth)acrylate, 2-ethoxyethyl (meth)acrylate, 3-methoxybutyl (meth)acrylate, 2-hydroxyethyl (meth)acrylate, 2-hydroxypropyl (meth)acrylate, glycidyl (meth)acrylate, 2-aminoethyl (meth)acrylate, γ-(methacryloyloxypropyl)tetramethylsilane, an ethylene oxide adduct of (meth)acrylate, (meth) acrylate-terminated polyethylene glycol on both ends, (meth)acrylate-terminated polypropylene glycol on both ends, (meth)acrylate-terminated polybutylene glycol on both ends, trifluoromethylmethyl (meth)acrylate, 2-trifluoromethylethyl (meth)acrylate, 2-perfluoroethylethyl (meth) acrylate, 2-perfluoroethyl-2-perfluorobutylethyl (meth)acrylate, perfluoroethyl (meth)acrylate, perfluoromethyl (meth) acrylate, difluoromethylmethyl (meth)acrylate, perfluoromethyl-perfluoroethylmethyl (meth)acrylate, 2-perfluorohexylethyl (meth)acrylate, 2-perfluorodecylethyl (meth)acrylate, and 2-perfluorohexadecylethyl (meth)acrylate;

an aromatic vinyl monomer such as styrene, vinyltoluene, α-methylstyrene, chlorstyrene, p-methoxystyrene, p-butoxystyrene, styrenesulfonic acid and a salt thereof;

a silicon-containing monomer such as vinyl trimethoxysilane and vinyl triethoxysilane;

maleic anhydride, maleic acid and a monoalkylester and a dialkylester of maleic acid;

fumaric acid and a monoalkylester and a dialkylester of fumaric acid;

a maleimide-based monomer such as maleimide, N-methylmaleimide, N-ethylmaleimide, N-propylmaleimide, N-butylmaleimide, N-hexylmaleimide, N-octylmaleimide, N-dodecylmaleimide, N-stearylmaleimide, N-phenylmaleimide and N-cyclohexylmaleimide;

a vinyl cyanide monomer such as acrylonitrile and methacrylonitrile;

an amide group-containing monomer such as acrylamide and methacrylamide;

a vinyl ester such as vinyl acetate, vinyl propionate, vinyl pivalate, vinyl benzoate and vinyl cinnamate;

an alkene such as ethylene and propylene;

a halogen-containing alkene such as perfluoroethylene, perfluoropropylene, vinylidene fluoride, vinyl chloride, vinylidene chloride, and allyl chloride;

a conjugated diene such as butadiene and isoprene; and allyl alcohol.

They may be used alone or two or more of them may be used in combination.

Among them, in terms of physical properties of the product, an aromatic vinyl monomer, a (meth)acrylate ester and a vinyl cyanide monomer may be preferred with a (meth)acrylate ester and a vinyl cyanide monomer being more preferred. As used herein the term "(meth)acrylate" refers to "methacrylate" or "acrylate."

The polymerization of a vinyl monomer using the compound of the present invention permits polymerization control in radical polymerization, and enables the synthesis of a polymer and a block copolymer having narrow molecular weight distribution.

As a polymerization method, there can be used mass polymerization, solution polymerization, suspension polymerization or emulsion polymerization. Among them, because of the surface-activating ability to be carried by the compound of the present invention, suspension polymerization or emulsion polymerization may be preferred, and because of the ease of removing heat during polymerization, emulsion polymerization may be more preferred.

In emulsion polymerization, generally an emulsifying agent and a dispersion stabilizer may be used. Since a RAFT agent having a HLB value of 3 or more determined by Griffin's method for $R^1$ and $R^3$ is used in the polymerization method of the present invention, said RAFT agent can also be used as an emulsifying agent or a dispersion stabilizer, but in addition to the RAFT agent of the present invention, there can also be used a known emulsifying agent such as an anionic emulsifying agent, a nonionic emulsifying agent and a cationic emulsifying agent, or dispersion stabilizer. They may be used alone or two or more of them may be used in combination.

As an emulsifying agent, there can be mentioned a sulfate-based emulsifying agent such as sodium lauryl sulfate, a sulfonate-based emulsifying agent such as sodium alkylbenzenesulfonate and sodium alkyldiphenylethersulfonate, a sulfosuccinic acid-based emulsifying agent, an amino group-containing emulsifying agent, and a fatty acid-based emulsifying agent containing a monofatty acid and succinic acid.

An initiator used in emulsion polymerization may be one generally used in radical polymerization. As an initiator of radical polymerization, there can be mentioned, for example, an organic peroxide such as cumene hydroperoxide, t-butyl peroxide, benzoyl peroxide, t-butylperoxyisopropyl carbonate, di-t-butyl peroxide, t-butyl peroxylaurate, lauroyl peroxide, succinic peroxide, cyclohexanone peroxide and acetylacetone peroxide; a persulfate such as potassium persulfate and ammonium persulfate; an azo compound such as 2,2'-azobisisobutylnitrile and 2,2'-azobis-2,4-dimethylvaleronitrile, and the like. Among them, an organic peroxide or a persulfate may be preferred due to its high reactivity.

When an organic peroxide or a persulfate is used, a reducing agent may be used. As a reducing agent, there can be mentioned mixtures such as ferrous sulfate/glucose/sodium pyrophosphate, ferrous sulfate/dextrose/sodium pyrophosphate, and ferrous sulfate/sodium formaldehyde sulfoxylate/ethylenediamine acetate. The use of a reducing agent may be preferred since it can reduce polymerization temperature.

The amount used of a radical polymerization initiator may preferably be 0.005-10 parts by weight relative to 100 parts by weight of a vinyl monomer, more preferably 0.01-5 parts by weight, and most preferably 0.02-2 parts by weight. The lower limit of each of these ranges is significant in terms of polymerization speed and production efficiency. Also, the upper limit is significant in terms of increased molecular weight, impact resistance and powder characteristics of a polymer.

The polymerization temperature in radical polymerization of the present invention may preferably be −50-200° C., and more preferably 0-150° C. In emulsion polymerization which is a polymerization method using water as a medium, 40-120° C. may be preferred, and during polymerization at 100° C. or higher, polymerization may be carried out under pressure.

Also, radical polymerization using a compound of the present invention may be carried out without a solvent, or it may be radical polymerization using an organic solvent or water as a medium. An organic solvent is not specifically limited as long as it permits radical polymerization and does not impair the function as a RAFT agent by chemically changing a compound of the present invention.

In radical polymerization using a compound of the present invention, a vinyl monomer may be added dropwise to the polymerization system during radical polymerization, or radical polymerization may be carried out with batchwise addition.

When emulsion polymerization is carried out using a compound of the present invention, it may be preferred to prepare, before the addition of a vinyl monomer, an aqueous solution in which a compound of the present invention and an emulsifying agent has been mixed. By mixing before the addition of a vinyl monomer, a mixed micelle can be formed comprising the emulsifying agent and the compound of the present invention in an aqueous solution. After or during adding a vinyl monomer, or when vinyl monomer is added in a mixture, the compound of the present invention may be estimated to be incorporated preferentially in the vinyl monomer due to the problem of compatibility of the vinyl monomer and the compound of the present invention, and radical polymerization may proceed in a polymerization mechanism similar to a common radical mass polymerization.

Also, in radical polymerization using a compound of the present invention, synthesis of a block copolymer which is characteristic of controlled radical polymerization can be effected. In order to obtain a block copolymer, a second vinyl monomer may be added after the polymerization of a first vinyl monomer and polymerized to synthesize a diblock copolymer. Furthermore, after the polymerization of a second vinyl monomer, a third vinyl monomer may be added and polymerized to synthesize a triblock copolymer, and by further adding and polymerizing another vinyl monomer, a multiblock copolymer may also be synthesized. As a method for synthesizing a block copolymer, there can be mentioned, for example, a method in which each vinyl monomer may be added dropwise while adjusting the dropping speed thereof, and a method in which they may be added batchwise to form latex and then to initiate polymerization. Also, by using a mixture of different monomers as a first vinyl monomer, a copolymer block part derived from the first vinyl monomer may be a random copolymer part in which different first vinyl monomers are randomly polymerized with each other. Similarly, by using a mixture of different monomers as a second or third vinyl monomer, a copolymer block part derived from the second or third vinyl monomer may be a random copolymer part in which different second or third vinyl monomers are randomly polymerized with each other.

At this time, for stabilization of latex, the above emulsifying agent and dispersant other than the RAFT agent of the compound of the present invention may be added. Also, when a radical initiator is not present in the polymerization system, a radical initiator must be added to restart radical polymerization.

Also in polymerization using a compound of the present invention, a crosslinking monomer may be added as needed. For example, in order to confer rubber elasticity to the polymer obtained, n-butyl acrylate may be copolymerized with a small amount of allyl methacrylate, and polyethylene glycol, polypropylene glycol, polybutyleneglycol or the like having (meth)acrylate groups on both ends, and then methyl methacrylate may be polymerized, and thereby it is possible to adjust the polymerization process so as to assume a core-shell structure in which a core of n-butyl acrylate that polymerized while being crosslinked and its outer layer are coated with a polymer of methyl methacrylate as a shell.

As a method of recovering the polymer as powder from the polymer latex produced by the emulsion polymerization process, a method in which after a coagulation step in which the polymer latex is contacted with an aqueous coagulant solution and coagulated, it is washed with about 1-100 parts by weight of water, followed by a dehydration treatment such as filtration to prepare a wet powder, and further the wet powder is dried with a pressure dehydrator or a hot-air drier such as a fluidized drier may be preferred. The drying temperature and drying time at this time may be decided as appropriate depending on the type of the polymer.

As a coagulating agent to be used in the coagulation step, there can be mentioned, for example, a calcium salt such as calcium acetate and calcium chloride. When the polymer is an acrylic resin, it may preferably be calcium acetate, since in this case the formed body obtained has excellent anti-hot water whitening and the water content of the powder recovered may be reduced. The coagulant may be used alone or two or more of them may be used in combination.

The coagulant may be used as an aqueous solution. The concentration of an aqueous coagulant solution may preferably be 0.1% by weight or more, and more preferably 1% by weight or more, since it enables to stably coagulate and recover the polymer. Also, the concentration of an aqueous coagulant solution may preferably be 20% by weight or less, and more preferably 15% by weight or less, since it enables to reduce the amount of residual coagulant in the recovered polymer and gives an excellent anti-hot air whitening of the formed body obtained.

The amount of an aqueous coagulant solution used in the coagulation step may preferably be 10 parts by weight or more relative to 100 parts by weight of the polymer latex, and 500 parts by weight or less relative to 100 parts by weight of the polymer latex.

The temperature during the coagulation step may preferably be 30° C. or more and 100° C. or less. The contact time is not specifically limited.

Before recovering the polymer as a powder from the polymer latex, the polymer latex may be treated as needed with a filtering device charged with a filter material. The filtration treatment intends to remove scales produced during polymerization from the polymer latex, to remove contaminants, from the polymer latex, that entered into the polymerization feed or into the polymerization step from outside, and may be preferred in terms of forming a good formed body using a powder recovered from the polymer latex.

As a filtering device charged with a filter material, there can be mentioned one that employs a saclike mesh filter, a centrifuge-type filtering device that has a cylindrical filter material in the inside surface of a cylindrical filtering chamber and has stirring blades placed in the filtering material, and a filtering device in which a horizontally placed filter material moves in a horizontal circular motion and a vertical reciprocal motion with the surface of the filter material as the base. Among them, a filter device in which a horizontally placed filter material moves in a horizontal circular motion and vertical reciprocal motion may be preferred.

In the case of radical polymerization using an organic solvent, a known method of recovering a polymer can be used. Generally a method in which a polymer solution is added to a solvent in which the polymer obtained is insoluble, and the polymer is precipitated and recovered is known.

The polymer obtained in the above method has a functional group derived from a RAFT agent represented by the following general formula (3) or (4) at the end. Hereinafter this may be referred to as a "RAFT agent end." RAFT agent ends can be removed from the polymer obtained by treatment with an organic peroxide, a persulfate or an azo compound.

As an organic peroxide, a persulfate or an azo compound, there can be mentioned compounds illustrated as specific examples of the radical polymerization initiator.

By the elimination reaction of the RAFT agent end, a structure unit represented by the following general formula (3) or (4) can be removed from the polymer end.

[Chemical formula 7]

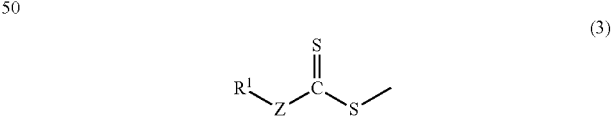

(3)

[Chemical formula 8]

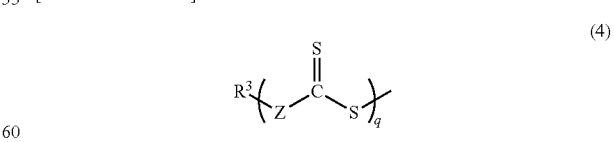

(4)

wherein, $R^1$ and $R^3$ each represent an organic group having a hydrophile-lipophile balance (HLB) determined by Griffin's method of 3 or more, Z represents a nitrogen atom, an oxygen atom, a sulfur atom, a methylene group, or an unsubstituted aromatic hydrocarbon group, R¹ represents, when Z is other than a sulfur atom, a monovalent organic group having one or more carbons, and said monovalent organic group may comprise at least one of a nitrogen atom, an oxygen atom, a sulfur atom, a halogen atom, a silicon atom and a phosphorous atom and may represent a high molecular weight substance, R¹ represents, when Z is a sulfur atom, a monovalent aliphatic hydrocarbon group or aromatic hydrocarbon group having one or more carbons that bind(s) to the sulfur atom at a primary carbon, and said monovalent hydrocarbon group may comprise at least one of a nitrogen atom, an oxygen atom, a sulfur atom, a halogen atom, a silicon atom and a phosphorous atom, or may represent a high molecular weight substance;

R³ represents, when Z is other than a sulfur atom, a q-valent organic group having one or more carbons, and said q-valent organic group may comprise at least one of a nitrogen atom, an oxygen atom, a sulfur atom, a halogen atom, a silicon atom and a phosphorous atom, or may represent a high molecular weight substance, and R³ represents, when Z is a sulfur atom, a monovalent aliphatic hydrocarbon group or aromatic hydrocarbon group having one or more carbons that bind(s) to the sulfur atom at a primary carbon; and q is an integer of 2 or more.

In order to allow the above compound to react with a RAFT agent-ended polymer, it is necessary to carry out the reaction at a temperature that allows the above compound to produce a radical. The temperature for producing a radical may be determined as appropriate depending on the compound used, and generally a half-life temperature of the above compound may be referred to, and may preferably be reacted at a temperature higher than that.

In addition to the above organic peroxide, persulfate, or azo compound, there can be used an oxidant such as m-chloroperbenzoic acid and sodium hypochlorite, or a nucleophilic reagent such as ammonium, a primary amine and a secondary amine.

By an elimination reaction of the RAFT agent end, when a nucleophilic reagent such as an oxidant and an amine is used, a structure unit represented by the following general formula (5) or (6) can be removed from the polymer end.

[Chemical formula 9]

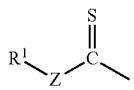

(5)

[Chemical formula 10]

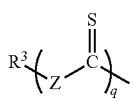

(6)

wherein, R¹ and R³ each represent an organic group having a hydrophile-lipophile balance (HLB) determined by Griffin's method of 3 or more, Z represents a nitrogen atom, an oxygen atom, a sulfur atom, a methylene group, or an unsubstituted aromatic hydrocarbon group, R¹ represents, when Z is other than a sulfur atom, a monovalent organic group having one or more carbons, and said monovalent organic group may comprise at least one of a nitrogen atom, an oxygen atom, a sulfur atom, a halogen atom, a silicon atom and a phosphorous atom and may represent a high molecular weight substance, R¹ represents, when Z is a sulfur atom, a monovalent aliphatic hydrocarbon group or aromatic hydrocarbon group having one or more carbons that bind(s) to the sulfur atom at a primary carbon, and said monovalent hydrocarbon group may comprise at least one of a nitrogen atom, an oxygen atom, a sulfur atom, a halogen atom, a silicon atom and a phosphorous atom, or may represent a high molecular weight substance;

R³ represents, when Z is other than a sulfur atom, a q-valent organic group having one or more carbons, and said q-valent organic group may comprise at least one of a nitrogen atom, an oxygen atom, a sulfur atom, a halogen atom, a silicon atom and a phosphorous atom, or may represent a high molecular weight substance, and R³ represents, when Z is a sulfur atom, a monovalent aliphatic hydrocarbon group or aromatic hydrocarbon group having one or more carbons that bind(s) to the sulfur atom at a primary carbon; and q is an integer of 2 or more.

The temperature at which the above compound is reacted to a RAFT agent-ended polymer may be determined as appropriate depending on the compound used, and generally may preferably be reacted at a temperature lower than the boiling point of the above compound.

The amount of an organic peroxide, a persulfate, an azo compound, an oxidant or a nucleophilic reagent to be used in the above method may affect the structure of the end of the polymer from which the RAFT agent end has been removed. When, relative to the amount of the RAFT agent end contained in the polymer, an equal or a smaller amount of the compound is used, a polymer having residual RAFT agent end can be obtained. In order to obtain a polymer in which the RAFT agent end has been removed, an equal amount to about 20-fold amount may preferably be added, and a 10-fold to 20-fold amount may be more preferred.

Thus, the structure of the end of the polymer in which the RAFT agent end has been removed by the above method may be different depending on the compound to be reacted.

When an organic peroxide, a persulfate or an azo compound is used, the structure of the end of the polymer may differ with the amount of the organic peroxide, the persulfate or the azo compound to be used. For example, an equal amount to about 10-fold amount the number of end of the polymer is used, it is known, double bonds may be formed at the end of the polymer after the RAFT agent end has been removed. When an about 10-fold to 20-fold amount is used, a polymer having no double bond at the end can be obtained by binding a radical at the end of the polymer obtained by removing the RAFT agent end and a end radical derived from the decomposition of an organic peroxide, a persulfate or an azo compound.

Details are described in Perrier et al.'s paper (Macromolecules, 2006, vol. 38, pp. 2033).

When a nucleophilic reagent such as an oxidizing agent and an amine is used, a polymer having a thiol group at the end can be obtained by using an equal amount to about 10-fold amount the number of end of the polymer. Using this thiol group, a ene-thiol reaction may be carried out or the metal surface and the thiol group at the end of the polymer may be reacted to prepare an organic/inorganic complex.

As a process for removing a RAFT agent end from a RAFT agent-ended polymer of the present invention, there can be mentioned a process of, after emulsion polymerization, recovering a powder of the RAFT agent-ended polymer using the above recovery method, then redissolving in a solvent, and adding an organic peroxide, a persulfate, an azo compound, an oxidizing agent, or a nucleophilic reagent to remove the RAFT agent end, a process of, after emulsion polymerization, adding the above compound to the system without recovering the polymer thereby to remove the RAFT agent end, and the like. Among them, for the ease of the process, the process of adding the above compound to the system without recovering the polymer after emulsion polymerization may be preferred.

When the RAFT agent end was removed from the polymer by conducting polymerization using any of (RAFT-1), (RAFT-2), (RAFT-5), (RAFT-6) and (RAFT-7) and acting an azo compound 2,2'-azobisisobutyronitrile (AIBN) thereon, the RAFT agent eliminated from the polymer has a structure identical with any of (RAFT-1), (RAFT-2), and (RAFT-5) to (RAFT-7). Thus, it is also possible to recover the eliminated RAFT agent after removing the RAFT agent from the polymer, and to reuse it.

As a method for recovering the eliminated RAFT agent after removing the RAFT agent from the polymer, there can be mentioned a method in which, after emulsion polymerization, the RAFT agent is removed from the polymer, the polymer is recovered by coagulating it, and the RAFT agent is recovered with an organic solvent from an aqueous solution used for coagulation after recovering the polymer. The RAFT agent thus recovered can be reused as long as it does not affect the polymerization controlling ability.

The thermoplastic resin composition of the present invention may comprise the polymer of the present invention, and as needed may be blended with another polymer material. Also, as needed, various known additives such as a lubricant, an antiblocking agent, a UV absorber, a photostabilizer, a plasticizer (phthalate, etc.), a stabilizer (2-t-butyl-6-(3-t-butyl-2-hydroxy-5-methylbenzyl)-4-methylphenylacrylate, etc.), a colorant (chrome orange, titanium oxide, etc.), a filler (calcium carbonate, clay, talc, etc.), an antioxidant (alkylphenol, an organic phosphite, etc.), a UV absorber (salicylate, benzotriazole, etc.), a fire retardant (a phosphate, antimony oxide, etc.), an antistatic, a lubricant, a foaming agent, and an antibacterial/antifungal agent may be added. The amount blended thereof may be determined as appropriate depending on the intended use. Known methods of blending can be used. For example, a mill roll, a Banbury mixer, a super mixer, a monoaxial or biaxial extruder, etc., may be used in mixing and kneading.

The thermoplastic resin composition of the present invention may be formed by a known molding method such as injection, melt extrusion and calendering. The forming temperature may be selected, as appropriate, depending on the thermal stability and molecular weight of the thermoplastic resin obtained, and may generally be formed at a temperature higher than the glass transition temperature of the thermoplastic resin.

The copolymer of the present invention may be useful as a thermoplastic resin composition, a thermal or light setting resin composition, a mordant resin composition and an adhesive resin composition making use of the fact that it is a block copolymer. The formed body of the present invention may be useful as a forming material such as film and sheet.

In addition to this, it is also possible to dissolve it in an organic solvent to form a film by the spincoat method or a solvent cast method.

It is also possible to use the thermoplastic resin composition of the present invention as a constituent of a resin composition for coating material. A coating material for a resin composition may be mixed with an organic solvent or may be constituted with solid components alone without using an organic solvent. The copolymer of the present invention an organic solvent and, as needed, various additives may be blended by a known method. In order to enhance a coating property, the resin composition for coating material may preferably be blended, as needed, with an organic solvent in which the thermoplastic resin of the present invention and, as needed, various additives are soluble.

As an organic solvent, there can be mentioned aromatic hydrocarbons such as toluene, xylene, "Swasol #1000" (trade name, manufactured by Maruzen Petrochemical Co., Ltd.), "Solvesso "150" (trade name, Exxon Chemicals Co., Ltd.) and "Supersol 1500" (trade name, manufactured by Nippon Petrochemicals Co., Ltd.); ketones such as methylethylketone and methylisobutylketone; esters such as ethyl acetate, n-butyl acetate, propyleneglycol monomethyletheracetate, "DBE" (trade name, manufactured by DuPont K.K.); alcohols such as n-butanol and isopropyl alcohol; glycol solvents such as ethyleneglycol monobutylether. Among these organic solvents, aromatic hydrocarbons may specifically be preferred because of their excellent workability. The organic solvent may be used alone or two or more of them may be used in combination.

When the thermoplastic resin composition of the present invention comprises hydroxyl group-containing monomer units, solvent resistance, water resistance, and weather resistance of coating film obtained can be enhanced by blending a melamine resin or an isocyanate compound as a crosslinking component to the resin composition for coating material.

As a specific example of the melamine resin, there can be mentioned a n-butylated melamine resin and a methylated melamine resin.

As an isocyanate compound, a polyisocyanate compound having a free isocyanate group and a blocked polyisocyanate compound may be mentioned. As specific examples, there can be mentioned aliphatic diisocyanates such as hexamethylene diisocyanate; cyclic aliphatic diisocyanates such as 4,4'-methylenebis(cyclohexylisocyanate); aromatic diisocyanates such as tolylene diisocyanate; adducts of an excess amount of said diisocyanate and a polyhydric alcohol or water; and polymers and biuret form of said diisocyanates.

An isocyanate compound may be blended with a monomer unit having a hydroxy group in a block copolymer at an equivalent ratio of NCO/OH=0.1/1 to 3/1.

Other examples of various additives include, for example, a gloss agent such as aluminum paste and mica; various stabilizing agents such as an antioxidant, a UV absorber, an anti-weather agent, an anti-radiation agent, and a thermal stabilizing agent; a coloring agent such as an inorganic pigment, an organic pigment and a dye; a conductivity-imparting agent such as carbon black and ferrite; a non-acrylic resin such as an inorganic filler, a lubricant, a plasticizer, an organic peroxide, a neutralizing agent, an alkyd resin, an epoxy resin, and a fibrinogen resin; and an auxiliary additive such as a surface-controlling agent, a curing catalyst, and a pigment sedimentation-preventing agent.

A resin composition for coating material can be coated by a known method. For example, there can be mentioned a method in which a resin composition for coating material or a resin composition for coating material to which an organic solvent has been added may be coated by blowing it to the substrate surface to a film thickness after drying of about 1-80 µm using a spray gun etc.

EXAMPLES

The present invention will now be explained in further details with reference to synthetic examples, Working Examples and Comparative Examples, but the present invention is not limited to these examples in any way. "Parts" and "%" in the examples refer to "parts by weight" and "% by weight," respectively.

1. Gas Chromatography (GC) Analysis

GC analysis was carried out under the following analytic condition, and from the peak area ratio, the purity of the RAFT agent and a precursor thereof and the concentration of impurities were determined.

Column: Capillary column DB-1 (manufactured by GL Sciences Inc., column length: 30 m, column inner diameter: 0.53 mm, film thickness in the capillary: 5 μm)

Carrier gas: Helium

Column temperature: 50° C. is maintained for 3 minutes, temperature is increased at 10° C./min, and 220° C. is maintained for 10 minutes Injection port temperature: 220° C.

Detector temperature: 220° C.

Detector: FID

2. Polymerization Conversion Ratio

The polymerization conversion ratio was calculated by measuring the solid of latex. The solid was determined as follows:

In an aluminum cup, a solution after the desired period of polymerization time was weighed out, which was set as (y'), dried at 80° C. for 12 hours, and the weight of the solid was measured, which was set as (x'). From the ratio (x/y) of the total weight (x) of the vinyl monomer and the RAFT agent contained during polymerization and the weight (y) of the total feed, a theoretical solid when 100% was polymerized was calculated, and from the ratio of the solid after drying (x'/y') and (x/y), the polymerization conversion ratio was calculated.

Polymerization conversion ratio=100×{(x'/y')/(x/y)}

3. The Number Average Molecular Weight and Molecular Weight Distribution of the Polymer Number average molecular weight (Mn), weight average molecular weight (Mw) and molecular weight distribution (Mw/Mn) were determined by gel permeation chromatography (GPC) with methyl polymethacrylate as the standard.

Instrument: HLC-8220 (manufactured by Tosoh Corp.)

Column: TSK GUARD COLUMN SUPER HZ-L (manufactured by Tosoh Corp., 4.6×35 mm), TSK-GEL SUPER HZM-N (manufactured by Tosoh Corp., 6.0×150 mm)×2 connected in series Eluent: Chloroform Measuring temperature: 40° C.

Flow rate: 0.6 mL/min

4. Identification of Compound and Confirmation of the presence of an end RAFT agent For measurement, $^1$H-NMR (manufactured by Jeol Ltd., JNM-EX270) was used.

The compound was dissolved in deuterated chloroform, and tetramethoxysilane in deuterated chloroform was used as an internal standard. The measuring temperature was 25° C. and the number of addition was 16.

For the polymer after the end treatment step, the polymer was dissolved in deuterated chloroform, and using tetramethoxysilane in deuterated chloroform as an internal standard, the presence of the RAFT agent was confirmed from the presence of aromatic peaks derived from the RAFT agent.

Working Example 1

Synthesis of Polyethylene Glycol (PEG)-RAFT-1

In a 200 ml round-bottomed flask, 17.3 g (100 mmol) of 4-bromophenol, 0.01 g of p-toluenesulfonic acid monohydrate, and 100 ml of dichloromethane were introduced. After cooling to 0° C., 9.25 g (110 mmol) of dihydropyran (DHP) was added dropwise. After stirring for 3 hours, the reaction mixture was concentrated, and purified by silica gel chromatography (eluted with a mixed solvent of ethyl acetate: n-hexane=1:5 (vol/vol)) to obtain 21.3 g of 2-(4-bromophenoxy)tetrahydro-2H-pyran (precursor A) (yield: 83.0%).

Then, into a 500 ml four-mouth flask equipped with a condenser and a thermometer, 1.95 g (80 mmol) of magnesium, 100 ml of dehydrated tetrahydrofuran (THF) and 0.02 g of iodine were introduced. Then, a dropping funnel containing 20.6 g (80 mmol) of previously synthesized precursor A and another dropping funnel containing 14.2 g (88 mmol by assuming a purity of 92%) of bromoisobutyronitrile were prepared, and the inside of the reaction system was replaced with argon. 20-30% of the precursor A was introduced at room temperature, and after starting the Grignard reaction, the remaining precursor A was added dropwise while maintaining the reaction temperature at 50-60° C.

After the dropwise addition was over and stirring at 35-40° C. for 1 hour, 6.70 g (88 mmol) of carbon bisulfide was added dropwise while keeping the inner temperature at 45° C. or less. After the dropwise addition was over, temperature was maintained at 38-40° C. for 1 hour, and then bromoisobutyronitrile was slowly added dropwise. After the dropwise addition was over, the temperature of the reaction mixture was increased to 56° C. and stirring was continued for 72 hours.

72 hours later, ice water was introduced into the reaction mixture, and after evaporating THF under reduced pressure from the reaction mixture, the reaction mixture was extracted twice with 200 ml of diethylether. The extract was dried with magnesium sulfate, and then concentrated. To the crude product obtained, 100 ml of THF was added. After cooling to 0° C., 0.1 ml of 3.6% hydrochloric acid was added and continued to stir until tetrahydropyranylether was deprotected. After the reaction was over, sodium carbonate was added to the reaction mixture to neutralize hydrochloric acid and concentrated. By purifying by silica gel chromatography (eluted with a mixed solvent of ethyl acetate:n-hexane=1:5 (vol/vol)), 10.6 g of 2-cyanoprop-2-yl-(4-hydroxy)dithiobenzoate (precursor B) was obtained (yield: 55.7%).

To a round-bottomed flask equipped with a condenser, 45 g (60 mmol) of PEG monomethylether of Mn 750, 20 g of pyridine and 200 g of toluene were added, and after adding 30 g (300 mmol) of succinic anhydride was added, it was heated to 80° C. and reacted for 72 hours. Seventy two hours later, the reaction mixture was cooled, and the unreacted succinic anhydride that deposited was filtered off. Then, water was added to the residue obtained by evaporating toluene and pyridine under reduced pressure, insoluble matters were filtered off. After the procedure of concentrating the filtrate under reduced pressure and then adding water to concentrate again was carried out for a total of 3 times, toluene was added to the residue to remove residual water by azeotropic distillation, and thus 50 g of crude monomethoxypolyethylene glycol succinate ester (precursor C) was obtained.

4.00 g (4.7 mmol) of precursor C and 1.13 g (4.7 mmol) of previously synthesized precursor B were dissolved in 10 g of dichloromethane, to which 1.1 g (5.3 mmol) of N,N'-dicyclohexylcarbodiimide and 0.1 g of N,N-dimethylaminopyridine were added and then reacted at 50-55° C. for 48 hours.

Forty eight hours later, the reaction mixture was cooled to room temperature, and the solid deposited was filtered off. After concentrating the filtrate, a mixed solvent of n-hexane:

diethylether=1:1 was added. After stirring for about 30 minutes at room temperature and allowing to stand, the supernatant was decanted. The residue was concentrated under reduced pressure to obtain 4.7 g of PEG-RAFT-1 (yield: 92.0%).

[Chemical formula 11]

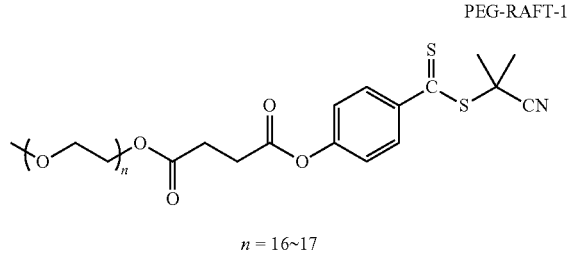

PEG-RAFT-1

$n = 16\sim17$ $^1$H-NMR (CDCl$_3$): δ (ppm): 1.94 (s, 6H), 2.79 (t, 2H), 2.90 (t, 2H), 3.38 (s, 3H), 3.63 (s, 62H), 4.27 (t, 2H), 7.15 (d, 2H), 7.96 (d, 2H)

The HLB value of R$^1$ of this PEG-RAFT-1 was about 17.3, and the HLB value of the PEG-RAFT-1 as a whole was about 13.8.

Working Example 2

Synthesis of PEG-RAFT-2

In a manner similar to Working Example 1 except that PEG monomethylether of Mn 2000 was used, PEG-RAFT-2 was obtained (yield: 89.0%).

The result of $^1$H-NMR was almost identical with the spectrum of PEG-RAFT-1 except that the integrated intensity of the peak observed at about 3.63 ppm was different. The HLB value of R$^1$ of this PEG-RAFT-2 was about 18.9, and the HLB value of the PEG-RAFT-2 as a whole was about 17.1.

[Chemical formula 12]

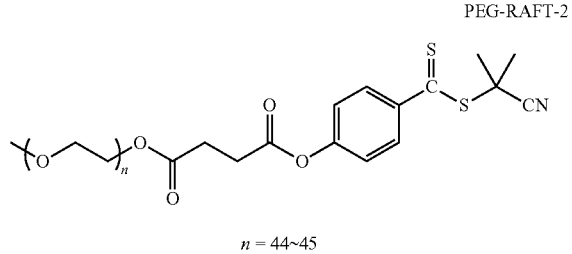

PEG-RAFT-2

$n = 44\sim45$

Working Example 3

Synthesis of PEG-RAFT-3

In a manner similar to Working Example 1, except that PEG monomethylether of Mn 5000 was used, PEG-RAFT-3 was obtained (yield: 78.5%).

The result of $^1$H-NMR was almost identical with the spectrum of PEG-RAFT-1 except that the integrated intensity of the peak observed at about 3.63 ppm was different. The HLB value of R$^1$ of this PEG-RAFT-3 was about 19.5, and the HLB value of the PEG-RAFT-3 as a whole was about 18.7.

[Chemical formula 13]

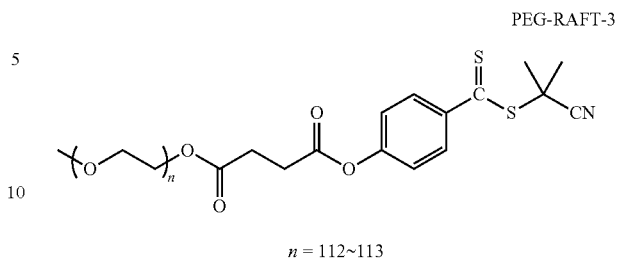

PEG-RAFT-3

$n = 112\sim113$

Working Example 4

Synthesis of anionic RAFT-1

In a 200 ml round-bottomed flask, 10.9 g (50 mmol) of 2-(4-bromophenoxy)ethanol, 0.01 g of p-toluenesulfonic acid monohydrate, and 50 ml of dichloromethane were introduced. After cooling to 0° C., 4.63 g (55 mmol) of DHP was added dropwise. After stirring for 3 hours, the reaction mixture was concentrated, and purified by silica gel chromatography (eluted with a mixed solvent of ethyl acetate: n-hexane=1:5 (vol/vol)) to obtain 13.7 g of 2-(4-bromophenoxy)ethoxy)tetrahydro-2H-pyran (precursor D) (yield: 91.0%).

Then, into a 200 ml four-mouth flask equipped with a condenser and a thermometer, 0.97 g (40 mmol) of magnesium, 30 ml of dehydrated THF and 0.01 g of iodine were introduced. A dropping funnel containing 12.0 g (40 mmol) of previously synthesized precursor D and another dropping funnel containing 7.07 g (44 mmol by assuming a purity of 92%) of bromoisobutyronitrile were prepared, and the atmosphere in the reaction system was replaced with argon. After adding dropwise precursor D while maintaining the reaction mixture at 50-60° C., it was stirred at 35-40° C. for 1 hour, and 3.35 g (44 mmol) of carbon bisulfide was added dropwise while keeping the inner temperature at 45° C. or less.

After the dropwise addition was over, temperature was maintained at 38-40° C. for 1 hour, and bromoisobutyronitrile was added dropwise. After the dropwise addition was over, the reaction temperature was increased to 56° C. and stirring was continued for 72 hours. Seventy two hours later, ice water was introduced into the reaction mixture, which was then concentrated and extracted twice with 200 ml of diethylether. The extract was dried with magnesium sulfate, then concentrated, and 200 ml of ethanol was added to the residue. After cooling to 0° C., 0.1 ml of 3.6% hydrochloric acid was added and continued to stir until tetrahydropyranylether was deprotected. After the reaction was over, the reaction mixture was concentrated, and purified by silica gel chromatography (eluted with a mixed solvent of ethyl acetate:n-hexane=1:1 (vol/vol)) to obtain 10.2 g of 2-cyanoprop-2-yl-{4-(2-hydroxy-ethoxy)}dithiobenzoate (precursor E) (yield: 91%).

To a round-bottomed flask, 1.16 g (4 mmol) of precursor E, 20 ml of THF, 10 ml of triethylamine and 0.4 g (4 mmol) of succinic anhydride were added, and reacted for 1 hour. One hour later, to this solution an aqueous solution having 0.4 g (4 mmol) of potassium bicarbonate dissolved in 5 ml of water was added. After stirring for 1 hour, the solvent was evaporated under reduced pressure. The residue was dissolved in 10 ml of water, and after extracting twice with 10 ml of ethyl acetate, the aqueous layer was taken out, and the solvent was evaporated under reduced pressure to obtain 1.34 g (3.2 mmol) of anionic RAFT-1 (yield: 79.8%).

[Chemical formula 14]

RAFT-1

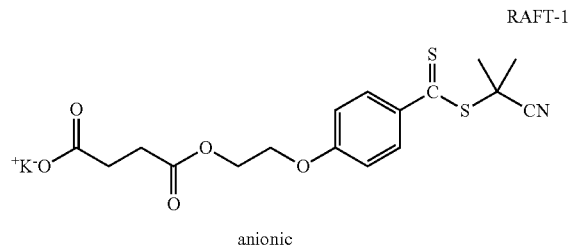

anionic $^1$H-NMR (D$_2$O): δ (ppm): (s, 6H), (t, 2H), (t, 2H), (t, 2H), (t, 2H), (d, 2H), (d, 2H)

The HLB value of R$^1$ of this anionic-RAFT-1 was about 8.3 (83.011/199.13), and the HLB value of the anionic-RAFT-1 as a whole was about 4.0.

Synthetic Example 1

Synthesis of RAFT-1

Into a 3000 ml four-mouth flask equipped with a condenser and a thermometer, 1790 g of carbon tetrachloride, 275 g (1.5 mol) of N-bromosuccinimide (NBS), 121.9 g (1.75 mol) of isobutyronitrile, and 3.75 g of AIBN were introduced, and the bath temperature was raised to 85° C. with an oil bath. After refluxing for 10 hours, the reaction mixture was cooled, the filtrate from which succinimide was removed was washed with a 10% aqueous solution of sodium bisulfite, and after further washing with water, dried with magnesium sulfate. After filtrating off the magnesium sulfate, a 102-130° C. fraction was aliquoted to obtain bromoisobutyronitrile.

Then, into a 2000 ml four-mouth flask equipped with a condenser and a thermometer, 24.3 g (1.0 mol) of magnesium, 750 ml of dehydrated THF and 0.1 g of iodine were introduced. Then, a dropping funnel containing 158 g (1.0 mmol) of bromobenzene and another dropping funnel containing 161 g (1.0 mmol by assuming a purity of 92%) of previously synthesized bromoisobutyronitrile were prepared, and the atmosphere in the reaction system was replaced with argon. After adding dropwise bromobenzene while maintaining the reaction mixture at 40° C., it was stirred at 37-40° C. for 1 hour, and 61 ml (1.0 mol) of carbon bisulfide was added dropwise at the inner temperature of 42° C. or less. After the dropwise addition was over and maintaining at 38-40° C. for 1 hour, bromoisobutyronitrile was added. After the dropwise addition was over, the reaction temperature was raised to 56° C., and stirring was continued for 24 hours.

Twenty four hours later, ice water was introduced into the reaction mixture, which was then concentrated and extracted twice with 1500 ml of diethylether. The extract was dried with magnesium sulfate, then concentrated, and purified by silica gel chromatography (using silica gel of 10-fold amount that of the crude product, eluted with a mixed solvent of ethyl acetate:n-hexane=1:20 (vol/vol)) to obtain 162.5 g of cyanoisopropyl dithiobenzoate (C$_6$H$_5$—C(S)S—C(CN)(CH$_3$)$_2$: RAFT-1) (yield: 72%).

Identification was carried out using $^1$H NMR, and assignment was made by referring to the values described in a reference (Polym. Int., 2000, Vol. 49, pp. 933-1001). Since corresponding to R$^1$ of this RAFT-1 is hydrogen atom (H—), and the HLB value becomes 0, RAFT-1 does not correspond to the compound of the present invention.

Synthetic Example 2

Synthesis of RAFT-2

Synthesis was carried out by referring to Rizzardo et al.'s paper (Macromolecules, 2007, Vol. 40, pp. 4446).

To 1000 ml of a diethylether solution in which 146 g (0.49 mol) of the previously synthesized sodium salt of n-dodecyl trithiocarbonate was dispersed, 63 g (0.25 mol) of iodine was added, stirred at room temperature for 1 hour, and sodium iodide produced was removed by filtration. An excess iodine was removed by washing with sodium thiosulfate, and after drying with magnesium sulfate, it was concentrated to obtain 120 g of a brown mixture.

After this mixture was dissolved in 1000 ml of ethyl acetate, 70 g (0.25 mol) of 4,4'-(4-cyanopentanoic acid) was added and refluxed for 24 hours. After evaporating the solvent, it was washed with hexane to dissolve the compound of interest. This solution was purified by silica gel chromatography (using silica gel of 10-fold amount that of the crude product, eluted with a mixed solvent of n-hexane: ethyl acetate=1:50 (vol/vol)) to obtain 89.2 g of C$_{12}$H$_{25}$—SC(S)S—C(CN)(CH$_3$)CH$_2$CH$_2$COOH: RAFT-2) (yield: 49%).

Identification of the compound was carried out based on the assignment described in the above reference. The HLB value of dodecyl group (C$_{12}$H$_{25}$—) corresponding to R$^1$ of this RAFT-1 is 0.

Working Example 5

Emulsion Polymerization of Methyl Methacrylate (MMA) Using PEG-RAFT-1-1

Into a separable flask equipped with a condenser and a stirrer unit, 2.85 parts of an anionic emulsifying agent (manufactured by Kao Corp., Pelex O-TP) and 1500 parts of distilled water were introduced, to which 1.67 part of PEG-RAFT-1 obtained in Working Example 1 was added and stirred at room temperature for 30 minutes. Then, 500 parts of MMA was added, and, in a nitrogen atmosphere, heated in a water bath to 80° C. under stirring. After raising the temperature to 80° C., an aqueous solution prepared by dissolving 0.5 part of potassium persulfate in 25 parts of distilled water was added in one motion, and then samples were collected at the desired times while stirring.

In the present Working Example, the ratio of the molar concentration of MMA and that of PEG-RAFT-1, i.e. [MMA]/[PEG-RAFT-1], is 3000 and a theoretical Mn when 100% of MMA was polymerized is about 300,000.

The solid of the samples collected at the desired sampling times was measured, the polymerization conversion ratio was determined, and Mn, Mw and Mw/Mn of the solid were determined by GPC. The results are shown in Table 5.

Working Example 6

Emulsion Polymerization of MMA Using PEG-RAFT-1-2

In a manner similar to Working Example 5, except that 8.33 parts of PEG-RAFT-1 in stead of 1.67 part was used, MMA was emulsion polymerized.

[MMA]/[PEG-RAFT-1] of the present Working Example is 600, and a theoretical Mn when 100% of MMA was polymerized is about 60,000.

The solid of the samples collected at the desired sampling times was measured, the polymerization conversion ratio was determined, and Mn, Mw and Mw/Mn of the solid were determined by GPC. The results are shown in Table 5.

Working Example 7

Emulsion Polymerization of MMA Using PEG-RAFT-1-3

In a manner similar to Working Example 5, except that the polymerization temperature was set at 50° C. in stead of 80° C. and 5.85 parts of a nonionic emulsifying agent (manufactured by Kao Corp., Emalgen 147) in stead of 2.85 parts of an anionic emulsifying agent (manufactured by Kao Corp., Pelex O-TP) was used, MMA was emulsion polymerized.

The solid of the samples collected at the desired sampling times was measured, the polymerization conversion ratio was determined, and Mn, Mw and Mw/Mn of the solid were determined by GPC. The results are shown in Table 6.

Working Example 8

Emulsion Polymerization of MMA Using PEG-RAFT-2-1

In a manner similar to Working Example 7, except that PEG-RAFT-2 (3.76 parts) synthesized in Working Example 2 in stead of PEG-RAFT-1 (1.67 part) was used, MMA was emulsion polymerized.

[MMA]/[PEG-RAFT-2] of the present Working Example is 3000, and a theoretical Mn when 100% of MMA was polymerized is about 300,000.

The solid of the samples collected at the desired sampling times was measured, the polymerization conversion ratio was determined, and Mn, Mw and Mw/Mn of the solid were determined by GPC. The results are shown in Table 6.

Working Example 9

Emulsion Polymerization of MMA Using PEG-RAFT-3-1

In a manner similar to Working Example 7, except that PEG-RAFT-3 (8.77 parts) synthesized in Working Example 3 in stead of PEG-RAFT-1 (1.67 part) was used, MMA was emulsion polymerized.

[MMA]/[PEG-RAFT-3] of the present Working Example is 3000, and a theoretical Mn when 100% of MMA was polymerized is about 300,000.

The solid of the samples collected at the desired sampling times was measured, the polymerization conversion ratio was determined, and Mn, Mw and Mw/Mn of the solid were determined by GPC. The results are shown in Table 6.

Comparative Example 1

Emulsion Polymerization of MMA Using RAFT-1-1

In a manner similar to Working Example 5, except that RAFT-1 (0.35 part) synthesized in Synthetic Example 1 in stead of PEG-RAFT-1 (1.67 part) was used, MMA was emulsion polymerized.

[MMA]/[RAFT-1] of the present Comparative Example is 3000, and a theoretical Mn when 100% of MMA was polymerized is about 300,000.

The solid of the samples collected at the desired sampling times was measured, the polymerization conversion ratio was determined, and Mn, Mw and Mw/Mn of the solid were determined by GPC. The results are shown in Table 7.

Comparative Example 2

Emulsion Polymerization of MMA Using RAFT-1-2

In a manner similar to Working Example 6, except that RAFT-1 (1.76 part) synthesized in Synthetic Example 1 in stead of PEG-RAFT-1 (8.33 parts) was used, MMA was emulsion polymerized.

[MMA]/[RAFT-1] of the present Comparative Example is 600, and a theoretical Mn when 100% of MMA was polymerized is about 60,000.

The solid of the samples collected at the desired sampling times was measured, the polymerization conversion ratio was determined, and Mn, Mw and Mw/Mn of the solid were determined by GPC. The results are shown in Table 7.

Comparative Example 3

Emulsion Polymerization of MMA Using RAFT-2-1

In a manner similar to Working Example 5, except that RAFT-2 (0.70 part) synthesized in Synthetic Example 2 in stead of PEG-RAFT-1 (1.67 part) was used, MMA was emulsion polymerized.

[MMA]/[RAFT-2] of the present Comparative Example is 3000, and a theoretical Mn when 100% of MMA was polymerized is about 300,000.

The solid of the samples collected at the desired sampling times was measured, the polymerization conversion ratio was determined, and Mn, Mw and Mw/Mn of the solid were determined by GPC. The results are shown in Table 7.

Comparative Example 4

Emulsion Polymerization of MMA Using RAFT-2-2

In a manner similar to Working Example 6, except that RAFT-2 (3.49 parts) synthesized in Synthetic Example 2 in stead of PEG-RAFT-1 (8.33 parts) was used, MMA was emulsion polymerized.

[MMA]/[RAFT-2] of the present Comparative Example is 600, and a theoretical Mn when 100% of MMA was polymerized is about 60,000.

The solid of the samples collected at the desired sampling times was measured, the polymerization conversion ratio was determined, and Mn, Mw and Mw/Mn of the solid were determined by GPC. The results are shown in Table 7.

Working Example 10

Emulsion Polymerization of MMA Using PEG-RAFT-1-4

In a manner similar to Working Example 7, except that the amount of PEG-RAFT-1 used was 11.9 parts and PEG- RAFT-1 previously dissolved in MMA was introduced in a separable flask, MMA was emulsion polymerized.

[MMA]/[PEG-RAFT-1] of the present Working Example is 420, and a theoretical Mn when 100% of MMA was polymerized is about 42,000.

The solid of the samples collected at the desired sampling times was measured, the polymerization conversion ratio was determined, and Mn, Mw and Mw/Mn of the solid were determined by GPC. The results are shown in Table 8.

Comparative Example 5

Emulsion Polymerization of MMA Using RAFT-1-3

In a manner similar to Working Example 10 except that 2.49 parts of RAFT-1 synthesized in Synthetic Example 1 in stead of 11.9 parts of PEG-RAFT-1 was added, MMA was emulsion polymerized.

[MMA]/[RAFT-1] of the present Comparative Example is 420, and a theoretical Mn when 100% of MMA was polymerized is about 42,000.

The solid of the samples collected at the desired sampling times was measured, the polymerization conversion ratio was determined, and Mn, Mw and Mw/Mn of the solid were determined by GPC. The results are shown in Table 8.

Working Example 11

Synthesis of MMA/n-butyl methacrylate (BMA) Block Copolymer Using PEG-RAFT-1-1

Into a separable flask equipped with a condenser and a stirrer unit, 6.0 parts of a nonionic emulsifying agent (manufactured by Kao Corp., Emalgen 147) and 120 parts of distilled water were introduced, to which 0.12 part of PEG-RAFT-1 obtained in Working Example 1, 0.3 part of potassium persulfate and 1.0 part of hexadecane as a dispersion assistant were added and stirred at room temperature for 30 minutes while purging with nitrogen. Then 15 parts of previously nitrogen-purged MMA was added dropwise, and heated to 50° C. in a water bath while stirring in a nitrogen atmosphere. Then samples were collected at the desired times while stirring. After confirming that MMA was consumed, 15 parts of previously nitrogen-purged BMA was added dropwise over 1.5 hours.

After the dropwise addition was over, and further heating for 1 hour, the consumption of BMA was confirmed by analyzing with gas chromatography and ended.

In the present Working Example, the ratio of the concentration of MMA and BMA and that of PEG-RAFT-1, i.e., [MMA+BMA]/[PEG-RAFT-1], is 2100 and a theoretical Mn when 100% of MMA and BMA was polymerized is about 270,000.

The solid of the samples collected at the desired sampling times was measured, the polymerization conversion ratio was determined, and Mn, Mw and Mw/Mn of the solid were determined by GPC. Mn was 280,000, Mw was 360,000 and Mw/Mn was 1.31.

Comparative Example 6

Emulsion Polymerization of MMA Using Mercaptan-1

In a manner similar to Working Example 5, except that n-dodecyl mercaptan (0.33 part) in stead of PEG-RAFT-1 (1.67 part) was used, MMA was emulsion polymerized.

The solid of the samples collected every 10 minutes was measured, the polymerization conversion ratio was determined, and Mn, Mw and Mw/Mn of the solid were determined by GPC. Polymerization was almost complete in 30 minutes, and the polymerization conversion ratio after 30 minutes was not less than 90%. However, irrespective of the polymerization time and the polymerization conversion ratio, Mn was about 100,000 and Mw/Mn was about 1.7, which were different from the behavior when controlled polymerization was progressing.

Working Example 12

Removal of RAFT Agent End

From an aqueous solution of the polymer obtained in Working Example 5, 1/10 was extracted, and to the extracted aqueous solution 0.27 part (10-fold equivalent relative to PEG-RAFT-1 end) of AIBN was added, and heated to 80° C. for 6 hours. Then, 200 parts of an aqueous solution in which calcium acetate was dissolved at 0.7% was warmed to 70° C. and stirred. Into this, an aqueous polymer solution was gradually added dropwise to effect coagulation.

After the deposit was separated and washed, it was dried at 75° C. for 24 hours to obtain a polymer. For the polymer obtained, the end was examined by NMR, and no aromatic peaks derived from the RAFT agent were observed at around 7.15 ppm and 7.96 ppm.

Comparative Example 7

Removal of RAFT Agent End

In a manner similar to Working Example 12, except that an aqueous solution of the polymer obtained in Comparative Example 1 was used, the removal of the AFT agent end was attempted. In a manner similar to Working Example 12, the polymer was recovered by coagulation, and the end was examined by NMR. Aromatic peaks derived from the RAFT agent were observe at around 7.15 ppm and 7.96 ppm.

Working Example 13

Injection Molding of a Resin from which the RAFT Agent End has been Removed

By a compact injection molding instrument (model "CS-183-MMX" manufactured by Custom Scientific Instruments Inc.), the polymer obtained in Working Example 12 was injection molded at 240° C. to obtain a formed body. The formed body was colorless and transparent, and no foaming was observed therein.

Comparative Example 8

Injection Molding of a resin Obtained Using RAFT-1

In a manner similar to Working Example 13, using a polymer recovered by coagulation from an aqueous solution obtained in Comparative Example 7, a formed body was obtained. The formed body was yellow and air bubbles derived from foaming were observed.

Working Example 14

Synthesis of Anionic RAFT-2

Into a 100 ml round bottomed flask, 0.93 g (6.2 mmol) of adipic acid, 1.4 g (5 mmol) of 2-cyanopropyl-2-yl-{4-(2- hydroxy-ethoxy)}dithiobenzoate (precursor E) and 60 ml of toluene were introduced, and dehydrated while evaporating toluene under reduced pressure. After adding 30 ml of dehydrated methylene chloride, 1.1 g (5.3 mmol) of dicyclohexyl carbodiimide and 50 mg of dimethylaminopyridine were added and reacted at room temperature for 6 hours. After the dicyclohexyl urea produced as a byproduct was filtered off, the reaction mixture was washed with 1 normal hydrochloric acid, dried with sodium sulfate, then concentrated under reduced pressure, and purified by silica gel chromatography (eluted with a mixed solvent of hexane:ethyl acetate=80:20 (vol/vol)) to obtain 1.6 g of 2-cyano-prop-2-yl-[4-(2-(6-carboxypentanoyloxy)-ethoxyl]dithiobenzoate (anionic RAFT-2) (yield: 78%).

[Chemical formula 15]

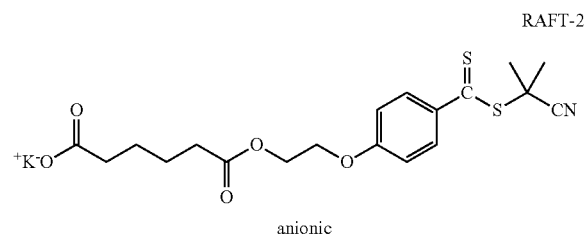

$^1$H-NMR (CDCl$_3$): 1.7 (ppm): (m, 4H), 1.9 (ppm): (s, 6H), 2.2 (ppm): (t, 2H), 2.3 (ppm): (t, 2H), 4.2 (ppm): (t, 2H), 4.5 (ppm): (t, 2H), 6.8 (ppm): (d, 2H), 7.9 (ppm): (d, 2H)

The HLB value of R$^1$ of this anionic RAFT-2 was about 7.31 (83.111/227.284), and the HLB value of the anionic RAFT-2 as a whole was about 3.71.

Working Example 15

Synthesis of Anionic RAFT-3

Into a 300 ml round bottomed flask, 3.0 g (22 mmol) of potassium carbonate crushed in a mortar, 6.1 g (35 mmol) of 4-bromphenol and 16.5 g (41 mmol) of 10-tetrapyranyloxy decanol p-toluenesulfonate were added, and, after adding 100 ml of acetone, was refluxed for 8 hours. After cooling to room temperature, water was added to end the reaction, and extracted twice with ethyl acetate. The ethyl acetate phase combined was washed with saturated saline, dried with sodium sulfate, and concentrated under reduced pressure. It was purified by column chromatography (eluted with a mixed solvent of ethyl acetate:n-hexane=20:80 (vol/vol))

using 300 g of silica gel to obtain 8.85 g of 4-(10-tetrapyranyloxydecanonoxy)phenylbromide (precursor F) (yield: 43%).

In a manner similar to Working Example 4, except that 7.4 g (18 mmol) of the precursor F obtained was used, a Grignard reaction was carried out at from room temperature to 86° C. After cooling to 40-56° C., 1.5 ml of carbon disulfide was added and reacted for 1 hour, and, while keeping the reaction mixture at 55° C., 3 g of α-bromoisobu-tylnitrile was added dropwise and the reaction was continued for 72 hours and then ice water was added to the reaction mixture, which was concentrated and extracted twice with 200 ml of diethylether. After drying the extract with magnesium sulfate, it was concentrated, 200 ml of methanol was added to the residue, and after cooling to 0° C., 0.1 ml of 3.6% hydrochloric acid was added and stirring was continued until tetrahydropyranylether was deprotected. After the reaction was over, the reaction mixture was concentrated and purified by silica gel column chromatography (eluted with a mixed solvent of ethyl acetate:n-hexane=1:1 (vol/vol)) to obtain 4 g of 2-cyanoprop-2-yl-{4-(2-hydroxydecanoxy)}dithiobenzoate (precursor G) (yield: 55%). 1.3 g (3.3 mmol) of precursor G, 0.35 g (3.5 mmol) of succinic anhydride and 0.2 g of triethylamine were dissolved in dehydrated toluene, to which 5 mg of dimethylaminopyridine was added and esterification reaction was carried out at room temperature. Since almost all precursor G disappeared 6 hours later with TLC, ethyl acetate and water were added to the reaction mixture and extracted. The organic phase was washed with dilute hydrochloric acid and saturated saline, then dried with magnesium sulfate, and concentrated under reduced pressure to obtain 1.68 g of anionic RAFT-3 (yield: 100%).

[Chemical formula 16]

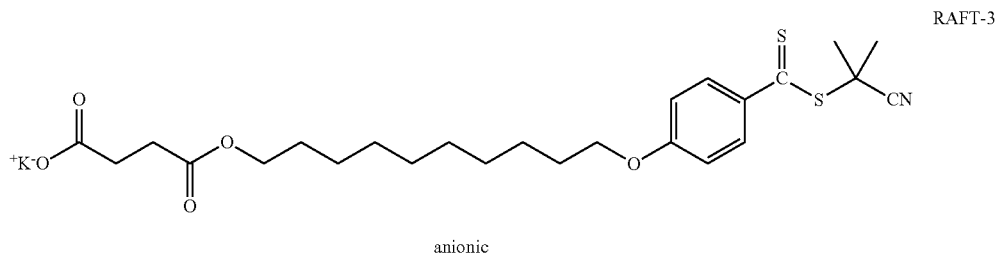

$^1$H-NMR (CDCl$_3$): 1.3-1.5 (ppm): (m, 16H), 1.9 (ppm): (s, 6H), 2.7 (ppm): (m, 4H), 4.0 (ppm): (t, 2H), 4.1 (ppm): (t, 2H), 6.8 (ppm): (d, 2H), 7.9 (ppm): (d, 2H)

The HLB value of R$^1$ of this anionic RAFT-3 was about 5.34 (83.111/311.446), and the HLB value of the anionic RAFT-3 as a whole was about 3.12.

Working Example 16

Synthesis of RAFT-1 Phosphate 2.06 g (13.4 mmol) of phosphorous oxychloride was introduced to a 30 ml round bottomed flask containing 2.5 g of THF, and cooled to −5° C. with a cryogen. 2.3 g (8.2 mmol) of 2-cyanopropyl-2-yl-{4-(2-hydroxy-ethoxy)}dithiobenzoate (precursor E) and 1.2 g (11.9 mmol) of triethylamine were dissolved in 10 g of THF, and added dropwise to the cooled solution of phosphorous oxychloride in THF. After the dropwise addition was over, stirring was continued for 2.5 hours under ice cooling, and then 3 g of dehydrated methanol was added and allowed to stand overnight at room temperature. The triethylamine chloride that deposited in the reaction mixture was filtered off, and the reaction mixture was frozen-concentrated. 1.7 g of RAFT-1 phosphate was obtained (yield: 60%).

[Chemical formula 17]

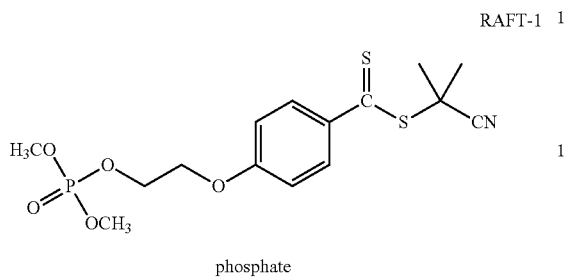

phosphate $^1$H-NMR (D$_2$O): δ (ppm): (s, xH)

The HLB value of R$^1$ of this RAFT-1 phosphate was about 14.8 (125.04/169.09), and the HLB value of the RAFT-1 phosphate as a whole was about 6.41.

Synthetic Example 3

Synthesis of RAFT-3

According to Mitsukami et al.'s method in Macromolecule, 2001, vol. 34, pp. 2248, di(dithibenzyl)disulfide was synthesized. Then, into a 100 ml round bottomed flask containing 30 ml of ethyl acetate, 3 g of di(dithibenzyl) disulfide and 3 g (11 mmol) of azobis(cyanovaleric acid) were introduced and purged with nitrogen, and then heated to reflux at 90° C. in an oil bath for 12 hours. After the reaction was over, it was concentrated under reduced pressure, purified by column chromatography using 200 g of silica gel to obtain 2.6 g of RAFT-3 (yield: 42.3%).

[Chemical formula 18]

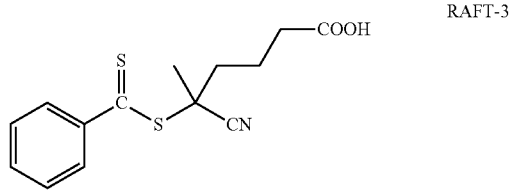

$^1$H-NMR (CDCl$_3$): 1.95 (ppm): (s, 3H), 2.40-2.80 (ppm): (m, 4H), 7.40 (ppm): (dd, 2H), 7.58 (ppm): (t, 1H), 7.89 (ppm): (d, 2H)

Since corresponding to R$^1$ of this RAFT-3 in Chemical formula (1) is hydrogen atom (H—), and the HLB value becomes 0, it does not correspond to the compound of the present invention. The HLB value of the RAFT-3 as a whole is about 5.02.

Working Example 17

Emulsion Polymerization of Isobutyl Methacrylate (IBMA) Using Anionic RAFT-1

6.25 parts of an anionic emulsifying agent (manufactured by Kao, Pelex O-TP), 1 part of sodium bicarbonate and 1000 parts of distilled water were introduced, and dissolved while purging with nitrogen. Separately a solution in which 1.7 part of anionic RAFT-1 obtained in Working Example X was dissolved in 125 parts of IBMA and 2.5 parts of hexadecane was added dropwise to an aqueous solution of an anionic emulsifying agent, and, after emulsifying with a homogenizer for 10 minutes, transferred to a baffled separable flask equipped with a condenser and a stirring unit and purged with nitrogen for 30 minutes. After raising the temperature of the flask to 60° C., 2.5 parts of potassium persulfate was added in one motion, and then samples were collected at the desired times while stirring.

In the present Working Example, the ratio of the concentration of IBMA and anionic RAFT-1, i.e., [IBMA]/[anionic RAFT-1], is 200, and a theoretical Mn when 100% of IBMA was polymerized is about 28,000.

The solid of the samples collected at the desired sampling times was measured, the polymerization conversion ratio was determined, and Mn, Mw and Mw/Mn of the solid were determined by GPC. The results are shown in Table 1.

TABLE 1

| Time (min) | conv(%) | Mn | Mw | Mw/Mn |
| --- | --- | --- | --- | --- |
| 100 | 11 | 12800 | 18000 | 1.41 |
| 145 | 21 | 16100 | 23000 | 1.43 |
| 190 | 38 | 20100 | 29100 | 1.45 |
| 240 | 67 | 41400 | 79900 | 1.93 |
| 290 | 69 | 44900 | 86300 | 1.92 |

Working Example 18

Emulsion Polymerization of MMA Using Anionic RAFT-2

In a manner similar to Working Example 17 except that 1.0 part of anionic RAFT-2 in stead of 6.25 parts of anionic RAFT-1 was used, MMA was emulsion polymerized.

[MMA]/[anionic RAFT-2] of the present Working Example is 510, and a theoretical Mn when 100% of MMA was polymerized is about 51,000.

The solid of the samples collected at the desired sampling times was measured, the polymerization conversion ratio was determined, and Mn, Mw and Mw/Mn of the solid were determined by GPC. The results are shown in Table 2.

TABLE 2

| Time (min) | conv(%) | Mn | Mw | Mw/Mn |
| --- | --- | --- | --- | --- |
| 35 | 4.4 | 9000 | 14700 | 1.63 |
| 65 | 36 | 52400 | 67600 | 1.29 |
| 95 | 81.3 | 85900 | 113400 | 1.32 |

Working Example 19

Emulsion Polymerization of MMA Using Anionic RAFT-3

In a manner similar to Working Example 17, except that 1.0 part of anionic RAFT-3 in stead of 6.25 parts of anionic RAFT-1 was used, MMA was emulsion polymerized.

[MMA]/[anionic RAFT-3] of the present Working Example is 610, and a theoretical Mn when 100% of MMA was polymerized is about 61,000.

The solid of the samples collected at the desired sampling times was measured, the polymerization conversion ratio was determined, and Mn, Mw and Mw/Mn of the solid were determined by GPC. The results are shown in Table 3.

TABLE 3

| Time (min) | conv(%) | Mn | Mw | Mw/Mn |
|---|---|---|---|---|
| 0 | 10.9 | 9600 | 16000 | 1.67 |
| 65 | 19.2 | 37500 | 42400 | 1.13 |
| 80 | 80.2 | 111000 | 138200 | 1.25 |

Working Example 20

Emulsion Polymerization of Styrene (St) Using PEG-RAFT-2

12.5 parts of PEG-RAFT-2 was introduced into 1790 parts of distilled water, and dissolved while purging with nitrogen. Separately 10 parts of hexadecane was dissolved in 200 parts of styrene, and the solution was added dropwise to an aqueous solution of PEG-RAFT-2, and, after emulsifying with a homogenizer for 10 minutes, transferred to a baffled separable flask equipped with a condenser and a stirring unit and purged with nitrogen for 30 minutes. After raising the temperature of the flask to 75° C., 5 parts of potassium persulfate was added in one motion, and then samples were collected at the desired times while stirring.

In the present Working Example, the ratio of the molar concentration of St and PEG-RAFT-2, i.e., [St]/[PEG-RAFT-2] is about 400, and a theoretical Mn when 100% of IBMA is polymerized is about 42,000.

The solid of the samples collected at the desired sampling times was measured, the polymerization conversion ratio was determined, and Mn, Mw and Mw/Mn of the solid were determined by GPC. The results are shown in Table 4.

TABLE 4

| Time (min) | conv(%) | Mn | Mw | Mw/Mn |
|---|---|---|---|---|
| 105 | 7 | 32500 | 48300 | 1.48 |
| 165 | 36.5 | 39400 | 56300 | 1.43 |
| 210 | 52 | 42700 | 61000 | 1.43 |
| 260 | 86.5 | 62000 | 120500 | 1.94 |

Figure 2:
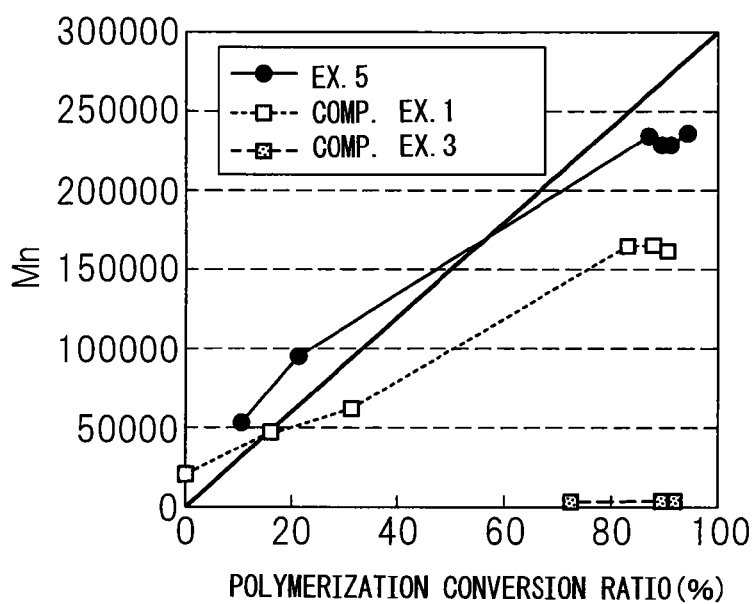
FIG. 2 A graph plotting the relationship between the polymerization conversion ratio and Mn obtained in Working Example 5, Comparative Example 1 and Comparative Example 3.
Figure 3:
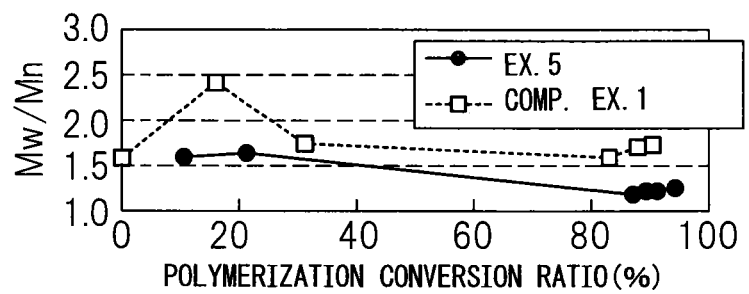
FIG. 3 A graph plotting the relationship between the polymerization conversion ratio and Mw/Mn obtained in Working Example 5 and Comparative Example 1.

FIGS. 1 to 3 illustrate plots of relationship between the polymerization time and the polymerization conversion ratio, relationship between the polymerization conversion ratio and Mn, and relationship between the polymerization conversion ratio and Mw/Mn obtained in Working Example 5, Comparative Example 1 and Comparative Example 3.

As can be seen from FIG. 1, the results of Working Example 5 that used PEG-RAFT-1 show that polymerization is almost complete at 60 minutes of polymerization time, and as can be seen from FIG. 2, Mn also increases together with the increase in the polymerization conversion ratio and is relatively consistent with the theoretical line. Also as can be seen from FIG. 3, Mw/Mn has been kept low irrespective of the increase in the polymerization conversion ratio, indicating that polymerization is being controlled.

On the other hand, the results of Comparative Example 1 that used RAFT-1 having no PEG chains demonstrate, as can be seen from FIG. 2, that while Mn increases together with the increase in the polymerization conversion ratio, it exhibits a behavior slightly off the theoretical line. Also, as can be seen from FIG. 3, Mw/Mn is not so narrow as the results in Working Example 5, indicating that the polymerization controlling ability is poorer than Working Example 5.

The results in Comparative Example 3 show, as can also be seen from Table 3, that molecular weight is kept low, a chart obtained by GPC shows multi peaks, and Mw/Mn gives a very broad result, indicating that polymerization is not controlled.

Figure 4:
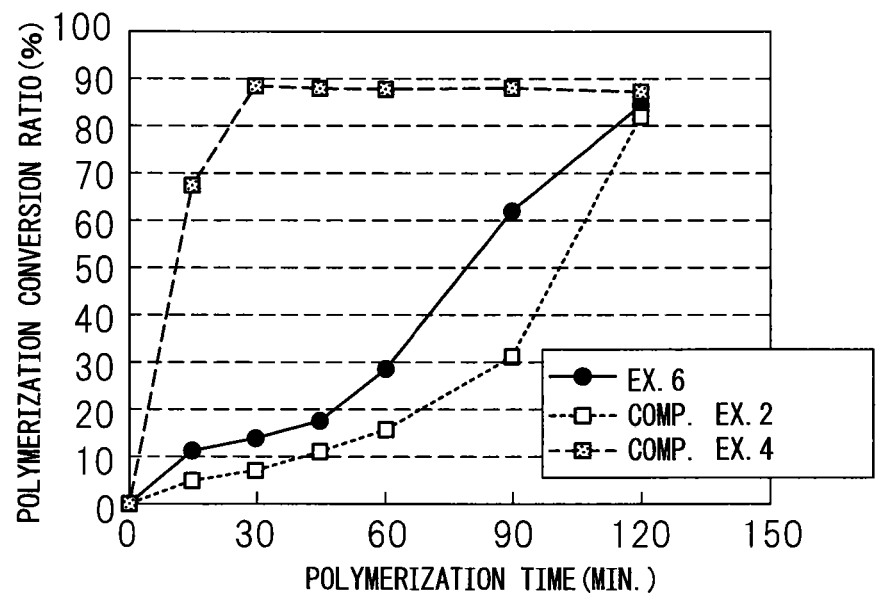
FIG. 4 A graph plotting the relationship between the polymerization time and the polymerization conversion ratio obtained in Working Example 6, Comparative Example 2 and Comparative Example 4.
Figure 5:
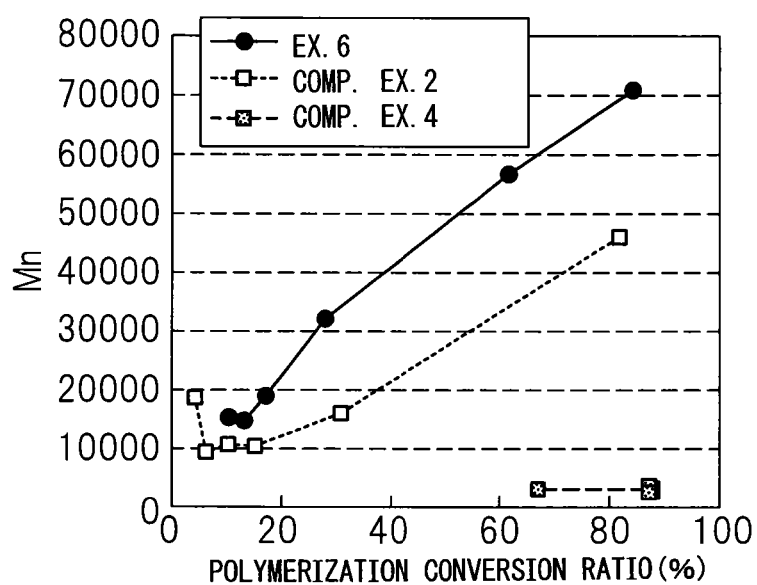
FIG. 5 A graph plotting the relationship between the polymerization conversion ratio and Mn obtained in Working Example 6, Comparative Example 2 and Comparative Example 4.
Figure 6:
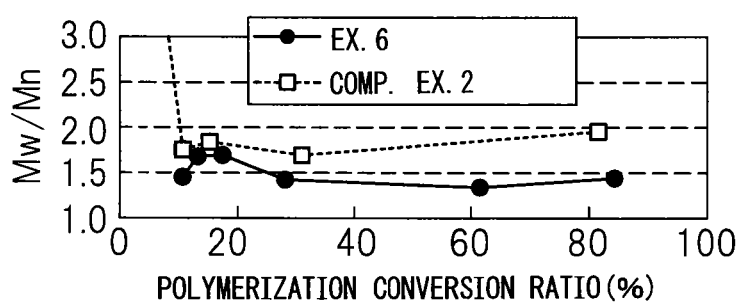
FIG. 6 A graph plotting the relationship between the polymerization conversion ratio and Mw/Mn obtained in Working Example 6 and Comparative Example 2.

FIGS. 4 to 6 illustrate plots of relationship between the polymerization time and the polymerization conversion ratio, relationship between the polymerization conversion ratio and Mn, and relationship between the polymerization conversion ratio and Mw/Mn obtained in Working Example 6, Comparative Example 2 and Comparative Example 4.

As can be seen from FIG. 4, the results of Working Example 6 that used PEG-RAFT-1 show that polymerization gradually proceeds until 120 minutes of polymerization time, and as can be seen from FIG. 5, Mn also increases together with the increase in the polymerization conversion ratio. Also as can be seen from FIG. 3, Mw/Mn is kept low irrespective of the increase in the polymerization conversion ratio, indicating that polymerization is being controlled.

On the other hand, the results of Comparative Example 2 that used RAFT-1 having no PEG chains demonstrate, as can be seen from FIG. 6, that Mw/Mn is not so narrow as the results in Working Example 6, indicating that the polymerization controlling ability is poorer than Working Example 6.

Figure 7:
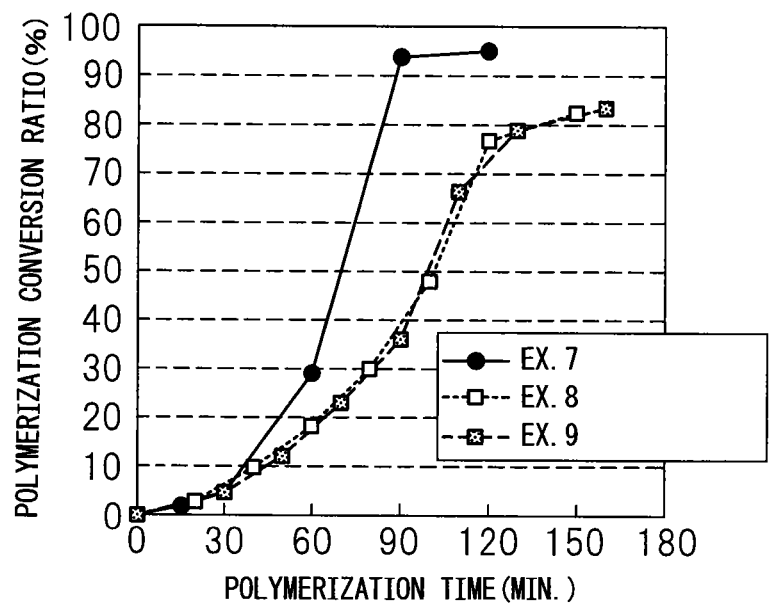
FIG. 7 A graph plotting the relationship between the polymerization time and the polymerization conversion ratio obtained in Working Examples 7 to 9.

The results in Comparative Example 4 show, as can also be seen from FIG. 7, similarly to the results of Comparative Example 3, that molecular weight is kept low, a chart obtained by GPC shows multi peaks, and Mw/Mn gives a very broad result, indicating that polymerization is not controlled.

Figure 8:
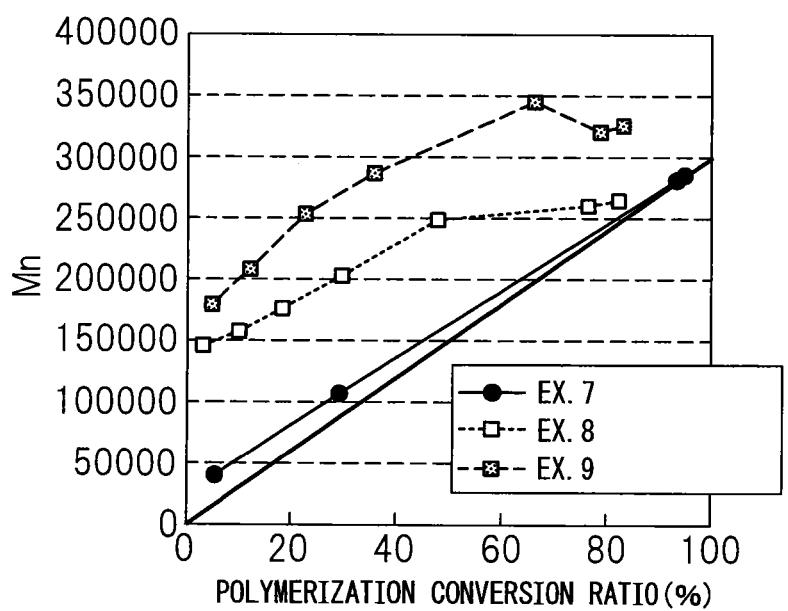
FIG. 8 A graph plotting the relationship between the polymerization conversion ratio and Mn obtained in Working Examples 7 to 9.
Figure 9:
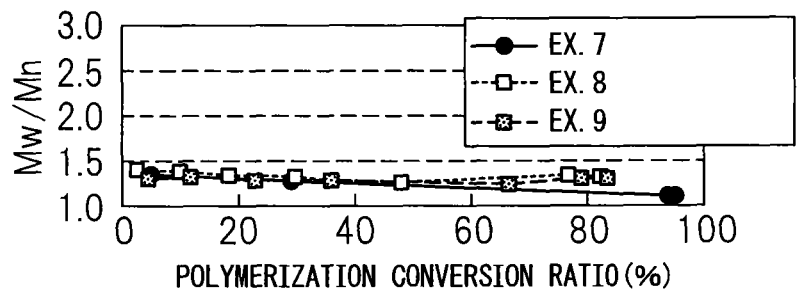
FIG. 9 A graph plotting the relationship between the polymerization conversion ratio and Mw/Mn obtained in Working Examples 7 to 9.

FIGS. 7 to 9 illustrate plots of relationship between the polymerization time and the polymerization conversion ratio, relationship between the polymerization conversion ratio and Mn, and relationship between the polymerization conversion ratio and Mw/Mn obtained in Working Examples 7 to 9.

As can be seen from FIG. 7, the results of Working Example 7 that used PEG-RAFT-1 in which PEG has a molecular weight of 750 show that polymerization is almost complete at 90 minutes of polymerization time, and Working Examples 8 and 9 that used PEG-RAFT-2 and 3 with a molecular weight of PEG being 2000 and 5000, respectively, show that the polymerization speed is slowed. Also as can be seen from FIG. 8, the results of Working Example 7 indicate that Mn also increases together with the increase in the polymerization conversion ratio and is relatively consistent with the theoretical line.

In Working Examples 8 and 9, molecular weight at the initial stage of polymerization is far off the theoretical line, but at the late stage of polymerization it exhibits a behavior of nearing the theoretical line. As can be seen from FIG. 9, the results of Working Examples 7 to 9 demonstrate that Mw/Mn is kept low irrespective of the increase in the polymerization conversion ratio, indicating that polymerization is being controlled.

Figure 10:
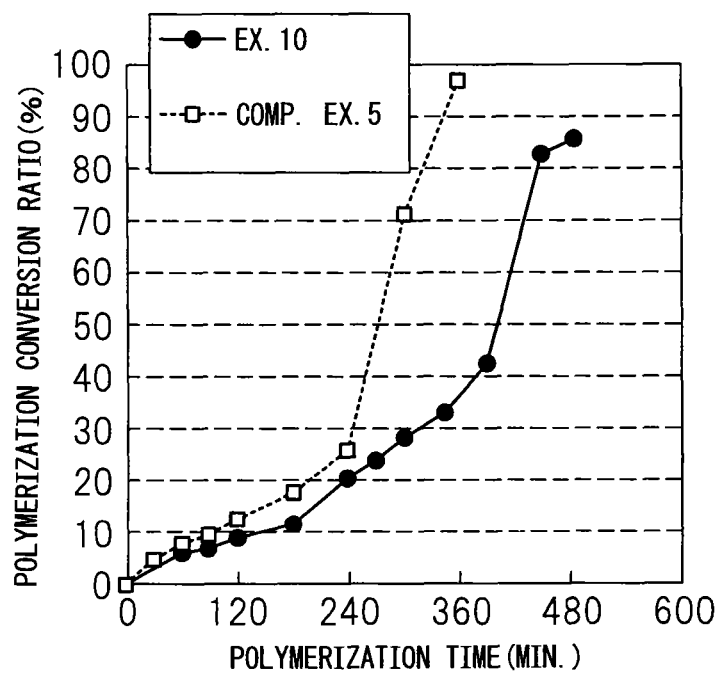
FIG. 10 A graph plotting the relationship between the polymerization time and the polymerization conversion ratio obtained in Working Example 10 and Comparative Example 5.
Figure 11:
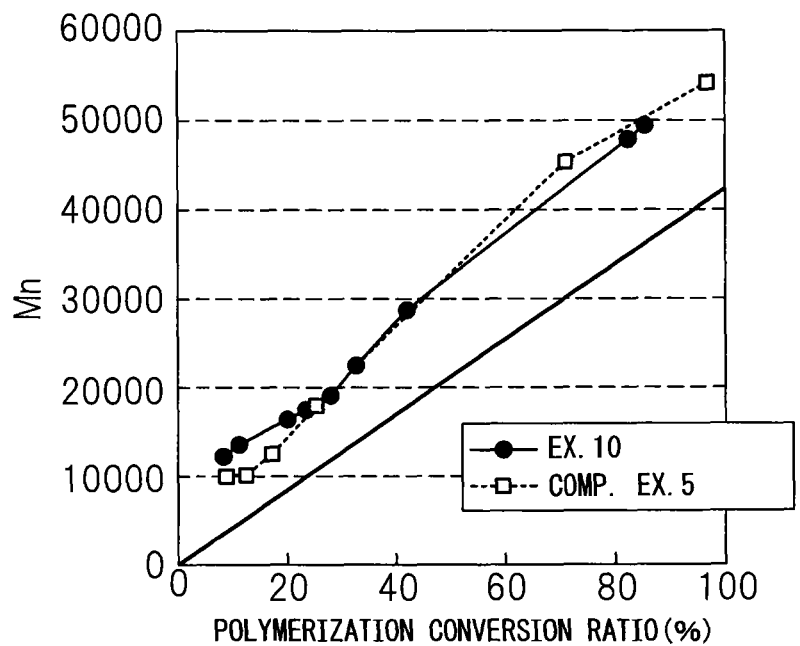
FIG. 11 A graph plotting the relationship between the polymerization conversion ratio and Mn obtained in Working Example 10 and Comparative Example 5.
Figure 12:
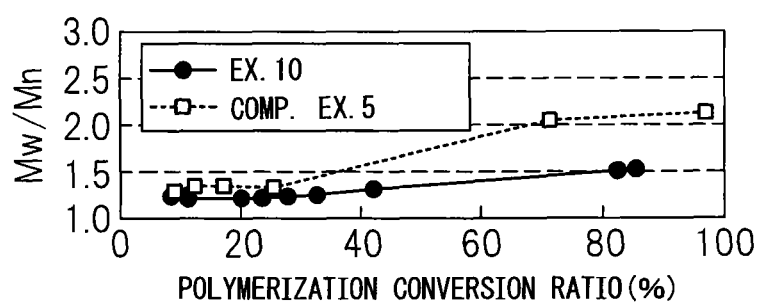
FIG. 12 A graph plotting the relationship between the polymerization conversion ratio and Mw/Mn obtained in Working Example 10 and Comparative Example 5.

FIGS. 10 to 12 illustrate plots of relationship between the polymerization time and the polymerization conversion ratio, relationship between the polymerization conversion ratio and Mn, and relationship between the polymerization conversion ratio and Mw/Mn obtained in Working Example 10 and Comparative Example 5. In Working Example 10 and Comparative Example 5, the RAFT agent previously dissolved in MMA was added to the polymerization system prior to polymerization, and an effect of the order of adding the RAFT agent on polymerization behavior was examined.

As can be seen from FIG. 11, the results of Working Example 10 and Comparative Example 5 that used PEG-RAFT-1 and RAFT-1 show that though Mn is off the theoretical line in both cases, it also increases together with the increase in the polymerization conversion ratio. Also as can be seen from FIG. 12, the results of Working Example 10 show that Mw/Mn is kept low irrespective of the increase in the polymerization conversion ratio, indicating that polymerization is being controlled, but in Comparative Example 5 the polymerization controlling ability is decreased with the increase in the polymerization conversion ratio.

TABLE 5

| | Working Example 5 | | | Working Example 6 | | |
|---|---|---|---|---|---|---|
| Polymerization time (min) | Polymerization conversion ratio (%) | Mn | Mw/Mn | Polymerization conversion ratio (%) | Mn | Mw/Mn |
| 0 | 0.0 | | | 0.0 | | |
| 15 | 10.8 | 52700 | 1.59 | 10.8 | 15100 | 1.45 |
| 30 | 21.5 | 95400 | 1.65 | 13.4 | 14600 | 1.66 |
| 45 | 87.4 | 234000 | 1.19 | 17.5 | 19000 | 1.69 |
| 60 | 89.6 | 229000 | 1.22 | 28.2 | 32000 | 1.41 |
| 90 | 91.4 | 229000 | 1.23 | 61.8 | 56600 | 1.33 |
| 120 | 94.4 | 236000 | 1.26 | 84.7 | 70700 | 1.42 |

TABLE 6

| Working Example 7 | | | | Working Example 8 | | | | Working Example 9 | | | |
|---|---|---|---|---|---|---|---|---|---|---|---|
| Polymerization time (min) | Polymerization conversion ratio (%) | Mn | Mw/Mn | Polymerization time (min) | Polymerization conversion ratio (%) | Mn | Mw/Mn | Polymerization time (min) | Polymerization conversion ratio (%) | Mn | Mw/Mn |
| 0 | 0.0 | | | 0 | 0.0 | | | 0 | 0.0 | | |
| 15 | 2.0 | | | 20 | 2.9 | 146000 | 1.38 | 30 | 4.6 | 179000 | 1.29 |
| 30 | 5.2 | 40700 | 1.34 | 40 | 9.9 | 158000 | 1.36 | 50 | 12.0 | 208000 | 1.31 |
| 60 | 29.1 | 107000 | 1.25 | 60 | 18.3 | 177000 | 1.33 | 70 | 22.9 | 254000 | 1.28 |
| 90 | 93.7 | 282000 | 1.09 | 80 | 29.9 | 203000 | 1.30 | 90 | 36.1 | 287000 | 1.26 |
| 120 | 94.9 | 285000 | 1.09 | 100 | 48.0 | 248000 | 1.26 | 110 | 66.4 | 344000 | 1.24 |
| | | | | 120 | 76.6 | 260000 | 1.33 | 130 | 78.9 | 320000 | 1.30 |
| | | | | 150 | 82.4 | 265000 | 1.30 | 160 | 83.3 | 325000 | 1.29 |

TABLE 7

| | Comparative Example 1 | | | Comparative Example 2 | | | Comparative Example 3 | | | Comparative Example 4 | | |
|---|---|---|---|---|---|---|---|---|---|---|---|---|
| Polymerization time (min) | Polymerization conversion ratio (%) | Mn | Mw/Mn | Polymerization conversion ratio (%) | Mn | Mw/Mn | Polymerization conversion ratio (%) | Mn | Mw/Mn | Polymerization conversion ratio (%) | Mn | Mw/Mn |
| 0 | 0.0 | | | 0.0 | | | 0.0 | | | 0.0 | | |
| 15 | 0.3 | 20500 | 1.59 | 4.6 | 18500 | 5.99 | 72.9 | 3300 | 60.9 | 67.4 | 3070 | 69.6 |
| 30 | 16.1 | 47500 | 2.42 | 6.5 | 9100 | 3.83 | 92.1 | 4200 | 53.0 | 88.1 | 3020 | 73.9 |
| 45 | 31.5 | 62000 | 1.76 | 10.7 | 10400 | 1.74 | 89.3 | 3090 | 58.9 | 87.7 | 2310 | 95.5 |
| 60 | 83.2 | 164000 | 1.60 | 15.5 | 10300 | 1.82 | 90.5 | 3830 | 57.3 | 87.4 | 3710 | 58.2 |
| 90 | 88.1 | 165000 | 1.71 | 31.1 | 15900 | 1.67 | 89.5 | 4670 | 51.9 | 88.0 | 2730 | 83.4 |
| 120 | 90.7 | 162000 | 1.73 | 82.0 | 46000 | 1.94 | 90.0 | 3860 | 45.6 | 87.3 | 2620 | 86.8 |

TABLE 8

| | Working Example 10 | | | | Comparative Example 5 | | |
|---|---|---|---|---|---|---|---|
| Polymerization time (min) | Polymerization conversion ratio (%) | Mn | Mw/Mn | Polymerization time (min) | Polymerization conversion ratio (%) | Mn | Mw/Mn |
| 0 | 0.0 | | | 0 | 0.0 | | |
| 60 | 5.7 | | | 30 | 4.3 | | |
| 90 | 6.7 | | | 60 | 7.6 | | |
| 120 | 8.5 | 12300 | 1.24 | 90 | 9.3 | 10100 | 1.30 |
| 180 | 11.3 | 13600 | 1.23 | 120 | 12.4 | 10300 | 1.34 |
| 240 | 20.2 | 16400 | 1.21 | 180 | 17.3 | 12500 | 1.34 |
| 270 | 23.6 | 17600 | 1.22 | 240 | 25.5 | 18000 | 1.33 |
| 300 | 28.1 | 19100 | 1.25 | 300 | 71.4 | 45400 | 2.06 |
| 345 | 32.7 | 22600 | 1.26 | 360 | 96.9 | 54100 | 2.13 |
| 390 | 42.3 | 28800 | 1.31 | | | | |
| 450 | 82.6 | 47900 | 1.51 | | | | |
| 485 | 85.6 | 49400 | 1.54 | | | | |

INDUSTRIAL APPLICABILITY

Emulsion polymerization using the compound of the present invention enables to control radical polymerization up to a high conversion ratio, and is an industrially excellent polymerization method. Also, from the polymer obtained, the RAFT agent can be easily removed, a colorless polymer can be obtained, and the polymer obtained can be used in optical applications.

The invention claimed is:

1. A method for radical-polymerizing a vinyl monomer, the method comprising:
   radical-polymerizing a vinyl monomer with the compound of formula (1):

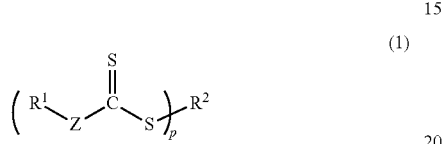

wherein:
   $R^1$ represents an organic group having a hydrophile-lipophile balance (HLB) determined by Griffin's method of 3 or more, wherein the organic group comprises polyethylene glycol, polypropylene glycol, or a polyethylene glycol/polypropylene glycol block copolymer and optionally comprising a carboxylic acid metal salt or sulfonic acid metal salt;
   Z represents an unsubstituted aromatic hydrocarbon group;
   when a plurality of $R^1$ are present, they may be the same or different;
   p is represented by an integer of 1 or more; and
   $R^2$ is a p-valent organic group having one or more carbons, and said p-valent organic group optionally comprises at least one selected from the group consisting of a nitrogen atom, an oxygen atom, a sulfur atom, a halogen atom, a silicon atom, a phosphorous atom, and a metal atom.

2. The method according to claim 1, wherein the radical polymerizing comprises emulsion polymerization.

3. A method for radical polymerizing a vinyl monomer, the method comprising:
   preparing an aqueous solution comprising a compound of formula (1) and an emulsifying agent in the absence of a vinyl monomer, to obtain a mixed micelle comprising the emulsifying agent and the compound of formula (1); and then
   adding a vinyl monomer to the aqueous solution comprising the mixed micelle and emulsion polymerizing the vinyl monomer.

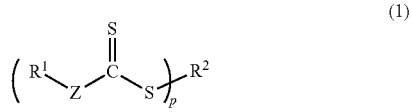

wherein:
   $R^1$ represents an organic group having a hydrophile-lipophile balance (HLB) determined by Griffin's method of 3 or more, wherein the organic group comprises polyethylene glycol, polypropylene glycol, or a polyethylene glycol/polypropylene glycol block copolymer and optionally comprising a carboxylic acid metal salt or sulfonic acid metal salt, wherein when a plurality of $R^1$ are present, they may be the same or different;
   Z represents an unsubstituted aromatic hydrocarbon group;
   p is represented by an integer of 1 or more; and
   $R^2$ is a p-valent organic group having one or more carbons, and said p-valent organic group optionally comprises at least one selected from the group consisting of a nitrogen atom, an oxygen atom, a sulfur atom, a halogen atom, a silicon atom, a phosphorous atom, and a metal atom.

4. The method according to claim 1, wherein after a first vinyl monomer or a mixture thereof is polymerized, a second vinyl monomer or a mixture thereof is newly added to produce a diblock copolymer.

5. The method according to claim 1, wherein after a first vinyl monomer or a mixture thereof is polymerized, a second vinyl monomer or a mixture thereof is added and polymerized, and then a vinyl monomer or a mixture thereof is added and polymerized in multi stages to produce a multiblock copolymer.

6. The method according to claim 1, wherein, in formula (1), $R^2$ is an unsubstituted hydrocarbon group, an unsubstituted aromatic hydrocarbon, or a cyano group.

7. The method according to claim 1, wherein, in formula (1), $R^2$ is a group of the formula:

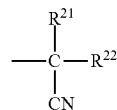

wherein, $R^{21}$ and $R^{22}$ are each independently alkyl groups having 1-8 carbon.

8. The method according to claim 7, wherein, $R^{21}$ and $R^{22}$ are each a methyl group.

9. The method of claim 1, wherein, in formula (1), p is 2.

10. The method of claim 1, wherein, in formula (1), Z is a phenyl group.

11. The method of claim 1, wherein, in formula (1), $R^1$ has an HLB value determined by Griffin's method of 11.1 or more.

12. The method of claim 1, wherein, in formula (1), $R^1$ has an HLB value determined by Griffi's method of 17.3 or more.

* * * * *